US012240827B2

(12) United States Patent
Ewin et al.

(10) Patent No.: US 12,240,827 B2
(45) Date of Patent: Mar. 4, 2025

(54) SEROTONIN 5-HT2B INHIBITORY COMPOUNDS

(71) Applicant: Zoetis Services LLC, Parsippany, NJ (US)

(72) Inventors: Richard Andrew Ewin, Kalamazoo, MI (US); Govindan Subramanian, Belle Mead, NJ (US); Jinxia (Nancy) Deng, Portage, MI (US)

(73) Assignee: Zoetis Services LLC, Parsippany, NJ (US)

( * ) Notice: Subject to any disclaimer, the term of this patent is extended or adjusted under 35 U.S.C. 154(b) by 727 days.

(21) Appl. No.: 17/441,340

(22) PCT Filed: Mar. 26, 2020

(86) PCT No.: PCT/US2020/024969

§ 371 (c)(1),
(2) Date: Sep. 21, 2021

(87) PCT Pub. No.: WO2020/198478

PCT Pub. Date: Oct. 1, 2020

(65) Prior Publication Data

US 2022/0162183 A1 May 26, 2022

Related U.S. Application Data

(60) Provisional application No. 62/825,051, filed on Mar. 28, 2019.

(51) Int. Cl.

| | |
|---|---|
| ***C07D 401/12*** | (2006.01) |
| ***C07D 401/04*** | (2006.01) |
| ***C07D 401/14*** | (2006.01) |
| ***C07D 405/14*** | (2006.01) |
| ***C07D 409/14*** | (2006.01) |

(52) U.S. Cl.

CPC ......... *C07D 401/12* (2013.01); *C07D 401/04* (2013.01); *C07D 401/14* (2013.01); *C07D 405/14* (2013.01); *C07D 409/14* (2013.01)

(58) Field of Classification Search

CPC .. C07D 401/12; C07D 401/04; C07D 401/14; C07D 405/14; C07D 409/14

USPC .......................................................... 514/318

See application file for complete search history.

(56) References Cited

U.S. PATENT DOCUMENTS 8,609,696 B2 * 12/2013 Cogan ....................... A61P 1/04 546/199
8,697,739 B2 4/2014 Barnes et al.
9,434,692 B2 9/2016 Xiong et al.

FOREIGN PATENT DOCUMENTS

WO WO-2010080357 A1 * 7/2010 ........... C07D 401/04

OTHER PUBLICATIONS

Moss et al. Bioorganic & Medicinal Chemistry Letters 2009, 19, pp. 2206-2210, A new class of 5-HT2B antagonists possesses favorable potency, selectivity, and rat pharmacokinetic properties. (Year: 2009).*

Moss, Neil, et al., "A new class of 5-HT2B antagonists possesses favorable potency, selectivity, and rat pharmacokinetic properties," Bioorganic & Medicinal Chemistry Letters 19 (2009) pp. 2206-2210.

* cited by examiner

*Primary Examiner* — Jared Barsky
*Assistant Examiner* — Liyuan Mou
(74) *Attorney, Agent, or Firm* — Paul M. Misiak

(57) ABSTRACT

The compounds of the invention, as described herein, are novel serotonin 5-HT2B antagonists useful for the treatment of myxomatous mitral valve degeneration (MMVD), congestive heart failure (CHF), and/or asymptomatic heart failure in animals, preferably canine.

7 Claims, No Drawings

SEROTONIN 5-HT2B INHIBITORY COMPOUNDS

CROSS-REFERENCE TO RELATED APPLICATIONS

This application is a US National Stage entry of International Application No. PCT/US2020/024969, filed Mar. 26, 2020, which claims the benefit of U.S. Provisional Application No. 62/825,051, filed Mar. 28, 2019.

FIELD OF THE INVENTION

This invention describes novel compounds that are serotonin 5-HT2B receptor antagonists useful for the treatment of mitral valve disease and congestive heart failure in animals. The invention also describes compositions comprising the compounds of the invention as well as methods of using said compounds for treating animals with mitral valve disease and congestive heart failure.

BACKGROUND

The serotonin 5-HT2B receptor was first characterized as the serotonogenic G protein-coupled receptors that controlled contraction in the rat stomach fundus (Clineschmidt, et al., 1985, J. Pharmacol. Exp. Ther., 235, 696). 5-HT2B has since been detected in human tissues including adipose tissue, central nervous system, heart, liver, intestine, lung, skeletal muscle, spleen and other organs and tissues (Kursar et al., 1994, Mal. Pharmacol., 46, 227; Sanden et al., 2000, Neurochem Int., 36, 427-435; Borman et al., 2002 Br. J. Pharmacol., 135, 1144; Schmuck et al., 1994, FEES Lett., 342, 85) and in dog tissues including the lungs, heart, smooth muscle, and brain (Bonaventure et.al, Eur J. Pharmacol. 2005 Apr. 25, 513(3) 181-192; Oyama et.al., J. Vet. Intern. Med. 2010, 24, 27-36). Modulators of 5-HT2B that include antagonists, partial antagonists, inverse agonists, and 5-HT2B desensitizers, may be used as treatments for disorders in these tissues in which activation of 5-HT2B has a direct or indirect role.

Control of serotonin (5-hydroxytryptamine, 5HT) levels and signaling is used to treat disorders of the central nervous system, intestinal contraction and motility, and vascular function. 5-HT has a role in vascular contraction and relaxation, and can impact vascular function, growth, and morphology. Wild-type mice develop symptoms of pulmonary arterial hypertension (PAH) under hypoxic conditions while 5-HT2B receptor knock-out mice do not, suggesting that modulation of 5-HT2B may alleviate PAH. The phenotype of 5-HT2B receptor knock-out mice demonstrates the importance of this receptor for heart development. Surviving mice possess under-developed hearts resulting from impaired myocyte proliferation (Nebigil, et al., 2001, Circulation, 103, 2973). Conversely, 5-HT2B over expression in mice leads to cardiac hypertrophy (Nebigil, et. Al., 2003, Circulation, 107 (25), 3223). Selective 5-HT2B antagonists prevent isoproterenol induced cardiac hypertrophy (Jaffre et al., 2004, Circulation, 110, 969). More recently, genomics data from a model of tachypacing-induced decompensatory heart failure in dogs showed an up-regulation of 5-HT2B mRNA (Ojaimi et.al., 2007, Physiol. Genomics 29, 76). Therefore, modulation of 5-HT2B may treat disorders associated with cardiac hypertrophy such as congestive heart failure. In fact, in both humans and experimental animal models, increased serotonin signaling can induce valvular interstitial cell (VIC) differentiation and myxomatous valve damage.

Myxomatous mitral valve disease (MMVD) is the leading cause of cardiovascular disease in dogs. MMVD causes incompetence of the mitral valve leading to mitral regurgitation which promotes sodium and water retention, activation of neurohormonal systems, volume overload, and eventual congestive heart failure (CHF). Synonymous MMVD medical terms used herein, include mitral valve disease (MVD), degenerative mitral valve disease (DMVD); chronic valve disease (CVD); chronic valvular heart disease (CVHD); and atrial ventricular valvular insufficiency (AVVI). The pathology of MMVD involves the differentiation and activation of the normally quiescent mitral VIC into a more active myofibroblast phenotype, which mediates many of the histological and molecular changes in the valve tissue. MMVD is present in approximately 30% of all dogs over the age of 10 years and is the most frequent cause of CHF in dogs. MMVD is most prevalent in small dogs, and breeds such as the Cavalier King Charles Spaniel, Chihuahua, Maltese, Pekinese, toy and miniature poodles. The natural history of the disease is one of adult onset, variable progression with aging, and eventual development of CHF in dogs with severe disease.

Current treatment for MMVD includes angiotensin enzyme inhibitors, diuretics, vasodilators, and positive inotropes which center on symptomatic relief rather than arresting disease progression. Further, some of these treatments pose additional adverse risks to the animal, for example: loss of appetite, lethargy, altered heart function (e.g., polarization) and renal damage. Compounds of the invention have been shown to modulate 5-HT with minimal or no effect on heart polarization. The compounds of the invention have a lower binding affinity to the $K_v11.1$ protein, which is an alpha subunit of a potassium ion channel coded by the hERG gene, than other 5-HT2B antagonists. The hERG (human Ether-a-go-go-Related Gene) ion channel is best known for its contribution to the electrical activity of the heart: the hERG channel mediates the repolarizing IKr current in the cardiac action potential, which helps coordinate the heart's beating. When this channels ability to conduct electrical current across the cell membrane is inhibited or compromised, either by application of drugs or by rare mutations, it can result in a potentially fatal disorder called long QT syndrome (LQTS). The LQTS is a condition which affects repolarization of the heart after a heartbeat. It results in an increased risk of an irregular heartbeat which can result in fainting or sudden death. A number of clinically successful drugs in the market have had the tendency to inhibit hERG while lengthening the QT and potentially leading to a fatal irregularity of the heartbeat (a ventricular tachyarrhythmia called torsades de pointes). This has made hERG inhibition an important anti-target that must be avoided during drug development for MMVD, CHF, and/or asymptomatic heart failure.

Given the anatomical and physiological similarities to the human heart, canine in-vivo heart models have been developed to correlate human and canine ERG. The development of said models depended, however, on information about canine potassium channels responsible for the establishment of IK currents. In this context, cERG (c-canine) was isolated and sequenced by reverse transcription (Pflugers Arch. 2001 May; 442(2):188-91. The complementary deoxyribonucleic acid derived cERG polypeptide was shown to consist of 1,158 amino acids, the sequence of which showed striking homology to human, rat and mouse ERG subunits (97%, 94% and 95% identity respectively). In highly conserved peptide domains like the PAS domain, the membrane-spanning segments S1, S3-S6 and the pore-forming region, there was 100% identity. Analysis of cERG transcription revealed abundant expression of cERG messenger ribonucleic acid in heart and brain and low expression in liver, spleen and kidney. Membrane currents recorded in *Xenopus* oocytes expressing cERG channels showed functional properties very similar to the human potassium channel hERG (h-human), which encodes the alpha-subunit of the cardiac rapidly activating, delayed rectifier (IKr) channel. As such, compounds to be developed for treating heart disease, for example, CHF and MMVD, need to have an affinity for the c5-HT2B receptor but not cERG.

WO2010/080357 describes certain serotonin 5-HT2B receptor inhibitors, including benzylimidazole and imidazole analogs. A number of these analogs were tested in comparative assays to assess the binding affinity to hERG and c5-HT2B. The compounds of the instant invention have shown a better safety profile than other known c5-HT2B antagonists since they have an affinity for the c5-HT2B receptor but not hERG. Therefore, the compounds of the invention may provide new and safer drug therapies to veterinarians for treating canine patients with MMVD to slow the progression of MMVD, CHF, and/or asymptomatic heart failure.

SUMMARY OF THE INVENTION

In one aspect of the invention, are novel serotonin 5-HT2B receptor antagonists useful for the treatment of mitral valve disease and congestive heart failure in animals, particularly canines. The compounds of the invention are novel 5-HT2B receptor antagonists with an affinity for the 5-HT2B receptor with minimal or not affinity for hERG. In one aspect of the invention, is a compound selected from the group consisting of:

(4-((1H-imidazol-2-yl)amino)piperidin-1-yl)(4'-fluoro-[1,1'-biphenyl]-4-yl)methanone;
(4-(1H-imidazol-2-yl)piperidin-1-yl)(3'-(methylsulfonyl)-[1,1'-biphenyl]-4-yl)methanone;
(4-(1H-imidazol-2-yl)piperidin-1-yl)(4'-(trifluoromethyl)-[1,1'-biphenyl]-4-yl)methanone;
(4-(5-methyl-1H-imidazol-2-yl)piperidin-1-yl)(4'-(trifluoromethyl)-[1,1'-biphenyl]-4-yl)methanone;
(4-(1H-indol-3-yl)phenyl)(4-(5-methyl-1H-imidazol-2-yl)piperidin-1-yl)methanone;
(4-(1H-indazol-3-yl)phenyl)(4-(5-methyl-1H-imidazol-2-yl)piperidin-1-yl)methanone;
(4-((1H-imidazol-2-yl)amino)piperidin-1-yl)(4'-(trifluoromethyl)-[1,1'-biphenyl]-4-yl)methanone;
(4-(1H-imidazol-2-yl)piperidin-1-yl)(4-phenoxyphenyl)methanone;
(4-(1H-imidazol-2-yl)piperidin-1-yl)(4-(phenylamino)phenyl)methanone;
(4-(1H-imidazol-2-yl)piperidin-1-yl)(3'-chloro-[1,1'-biphenyl]-4-yl)methanone,
trifluoroacetic acid salt;
(4-(1H-imidazol-2-yl)piperidin-1-yl)(6-phenylpyridin-3-yl)methanone, trifluoroacetic acid salt;
(4-((1H-imidazol-2-yl)methyl)piperidin-1-yl)(4'-(trifluoromethyl)-[1,1'-biphenyl]-4-yl)methanone, trifluoroacetic acid salt;
(4-(1H-imidazol-2-yl)piperidin-1-yl)(4-(benzo[d][1,3]dioxol-5-yl)phenyl)methanone, trifluoroacetic acid salt;
(4-(1H-imidazol-2-yl)piperidin-1-yl)(9H-carbazol-2-yl)methanone;
(4-(1H-imidazol-2-yl)piperidin-1-yl)(dibenzo[b,d]furan-3-yl)methanone, trifluoroacetic acid salt;
(4-(1H-imidazol-2-yl)piperidin-1-yl)(4'-(difluoromethyl)-[1,1'-biphenyl]-4-yl)methanone;
(4-(1H-imidazol-2-yl)piperidin-1-yl)(4-(1H-indol-4-yl)phenyl)methanone;
(4-(1H-imidazol-2-yl)piperidin-1-yl)(4-(1H-indol-1-yl)phenyl)methanone;
(4-(1H-imidazol-2-yl)piperidin-1-yl)(3'-(trifluoromethyl)-[1,1'-biphenyl]-4-yl)methanone;
(4-(1H-imidazol-2-yl)piperidin-1-yl)(4-(benzo[d][1,3]dioxol-4-yl)phenyl)methanone;
(4-(1H-imidazol-2-yl)piperidin-1-yl)(1-phenyl-1H-indol-5-yl)methanone;
(4-(1H-imidazol-2-yl)piperidin-1-yl)(4-(5-(trifluoromethyl)thiophen-2-yl)phenyl)methanone;
(4-(1H-imidazol-2-yl)piperidin-1-yl)(4-(1H-indol-3-yl)phenyl)methanone;
(4-(1H-imidazol-2-yl)piperidin-1-yl)(4-(1H-indazol-3-yl)phenyl)methanone;
(4-((1H-imidazol-2-yl)methyl)piperidin-1-yl)(4'-(difluoromethyl)-[1,1'-biphenyl]-4-yl)methanone;
(4-(4-methyl-1H-imidazol-2-yl)piperidin-1-yl)(4-(2-methyl-1H-indol-3-yl)phenyl)methanone;
(4-(1H-indol-6-yl)phenyl)(4-(5-methyl-1H-imidazol-2-yl)piperidin-1-yl)methanone;
(4-(1H-imidazol-2-yl)piperidin-1-yl)(1H,1'H-[3,4'-biindol]-6-yl)methanone;
[4-(1H-imidazol-2-yl)-1-piperidyl]-[3-(1H-indol-3-yl)-1H-indol-6-yl]methanone;
(4-(1H-imidazol-2-yl)piperidin-1-yl)(4-(1H-indol-2-yl)phenyl)methanone;
(4-(5-methyl-1H-imidazol-2-yl)piperidin-1-yl)(3-phenyl-1H-indol-6-yl)methanone;
(4-(1H-imidazol-2-yl)piperidin-1-yl)(3-phenyl-1H-indol-6-yl)methanone;
(4-((1H-imidazol-2-yl)amino)piperidin-1-yl)(4'-(difluoromethyl)-[1,1'-biphenyl]-4-yl)methanone; and
(4-(5-fluoro-1H-indol-3-yl)phenyl)(4-(4-methyl-1H-imidazol-2-yl)piperidin-1-yl)methanone; and veterinary acceptable salts thereof.

In another aspect of the invention is a compound selected from the group consisting of:

(4-((1H-imidazol-2-yl)amino)piperidin-1-yl)(4'-fluoro-[1,1'-biphenyl]-4-yl)methanone;
(4-(1H-imidazol-2-yl)piperidin-1-yl)(4'-(trifluoromethyl)-[1,1'-biphenyl]-4-yl)methanone;
(4-(5-methyl-1H-imidazol-2-yl)piperidin-1-yl)(4'-(trifluoromethyl)-[1,1'-biphenyl]-4-yl)methanone;
(4-(1H-indol-3-yl)phenyl)(4-(5-methyl-1H-imidazol-2-yl)piperidin-1-yl)methanone;
(4-(1H-indazol-3-yl)phenyl)(4-(5-methyl-1H-imidazol-2-yl)piperidin-1-yl)methanone;
(4-(1H-imidazol-2-yl)piperidin-1-yl)(4'-(difluoromethyl)-[1,1'-biphenyl]-4-yl)methanone;
(4-(1H-imidazol-2-yl)piperidin-1-yl)(4-(benzo[d][1,3]dioxol-4-yl)phenyl)methanone;
(4-(1H-imidazol-2-yl)piperidin-1-yl)(4-(1H-indol-3-yl)phenyl)methanone;
(4-((1H-imidazol-2-yl)methyl)piperidin-1-yl)(4'-(difluoromethyl)-[1,1'-biphenyl]-4-yl)methanone; and
(4-(4-methyl-1H-imidazol-2-yl)piperidin-1-yl)(4-(2-methyl-1H-indol-3-yl)phenyl)methanone; and veterinary acceptable salts thereof.

In another aspect of the invention is a compound selected from the group consisting of:

(4-((1H-imidazol-2-yl)amino)piperidin-1-yl)(4'-fluoro-[1,1'-biphenyl]-4-yl)methanone;
(4-(1H-indol-3-yl)phenyl)(4-(5-methyl-1H-imidazol-2-yl)piperidin-1-yl)methanone;
(4-(1H-indazol-3-yl)phenyl)(4-(5-methyl-1H-imidazol-2-yl)piperidin-1-yl)methanone;
(4-(1H-imidazol-2-yl)piperidin-1-yl)(4'-(difluoromethyl)-[1,1'-biphenyl]-4-yl)methanone;
(4-(1H-imidazol-2-yl)piperidin-1-yl)(4-(benzo[d][1,3]dioxol-4-yl)phenyl)methanone; and
(4-((1H-imidazol-2-yl)methyl)piperidin-1-yl)(4'-(difluoromethyl)-[1,1'-biphenyl]-4-yl)methanone; and veterinary acceptable salts thereof.

In another aspect of the invention is a compound selected from the group consisting of:
(4-(1H-indol-3-yl)phenyl)(4-(5-methyl-1H-imidazol-2-yl)piperidin-1-yl)methanone;
(4-(1H-indazol-3-yl)phenyl)(4-(5-methyl-1H-imidazol-2-yl)piperidin-1-yl)methanone;
(4-(1H-imidazol-2-yl)piperidin-1-yl)(4'-(difluoromethyl)-[1,1'-biphenyl]-4-yl)methanone; and
(4-((1H-imidazol-2-yl)methyl)piperidin-1-yl)(4'-(difluoromethyl)-[1,1'-biphenyl]-4-yl)methanone; and veterinary acceptable salts thereof.

In another aspect of the invention is a compound selected from
(4-(1H-indol-3-yl)phenyl)(4-(5-methyl-1H-imidazol-2-yl)piperidin-1-yl)methanone or 4-(1H-imidazol-2-yl)piperidin-1-yl)(4'-(difluoromethyl)-[1,1'-biphenyl]-4-yl)methanone; and veterinary acceptable salts thereof.

In another aspect of the invention is a compound that is (4-(1H-indol-3-yl)phenyl)(4-(5-methyl-1H-imidazol-2-yl)piperidin-1-yl)methanone; and veterinary acceptable salts thereof.

In another aspect of the invention is a compound that is 4-(1H-imidazol-2-yl)piperidin-1-yl)(4'-(difluoromethyl)-[1,1'-biphenyl]-4-yl)methanone; and veterinary acceptable salts thereof.

In one aspect of the invention, is a composition comprising a compound selected from the group consisting of:
(4-((1H-imidazol-2-yl)amino)piperidin-1-yl)(4'-fluoro-[1,1'-biphenyl]-4-yl)methanone;
(4-(1H-imidazol-2-yl)piperidin-1-yl)(3'-(methylsulfonyl)-[1,1'-biphenyl]-4-yl)methanone;
(4-(1H-imidazol-2-yl)piperidin-1-yl)(4'-(trifluoromethyl)-[1,1'-biphenyl]-4-yl)methanone;
(4-(5-methyl-1H-imidazol-2-yl)piperidin-1-yl)(4'-(trifluoromethyl)-[1,1'-biphenyl]-4-yl)methanone;
(4-(1H-indol-3-yl)phenyl)(4-(5-methyl-1H-imidazol-2-yl)piperidin-1-yl)methanone;
(4-(1H-indazol-3-yl)phenyl)(4-(5-methyl-1H-imidazol-2-yl)piperidin-1-yl)methanone;
(4-((1H-imidazol-2-yl)amino)piperidin-1-yl)(4'-(trifluoromethyl)-[1,1'-biphenyl]-4-yl)methanone;
(4-(1H-imidazol-2-yl)piperidin-1-yl)(4-phenoxyphenyl)methanone;
(4-(1H-imidazol-2-yl)piperidin-1-yl)(4-(phenylamino)phenyl)methanone;
(4-(1H-imidazol-2-yl)piperidin-1-yl)(3'-chloro-[1,1'-biphenyl]-4-yl)methanone,
trifluoroacetic acid salt;
(4-(1H-imidazol-2-yl)piperidin-1-yl)(6-phenylpyridin-3-yl)methanone, trifluoroacetic acid salt;
(4-((1H-imidazol-2-yl)methyl)piperidin-1-yl)(4'-(trifluoromethyl)-[1,1'-biphenyl]-4-yl)methanone, trifluoroacetic acid salt;
(4-(1H-imidazol-2-yl)piperidin-1-yl)(4-(benzo[d][1,3]dioxol-5-yl)phenyl)methanone,
trifluoroacetic acid salt;
(4-(1H-imidazol-2-yl)piperidin-1-yl)(9H-carbazol-2-yl)methanone;
(4-(1H-imidazol-2-yl)piperidin-1-yl)(dibenzo[b,d]furan-3-yl)methanone, trifluoroacetic acid salt;
(4-(1H-imidazol-2-yl)piperidin-1-yl)(4'-(difluoromethyl)-[1,1'-biphenyl]-4-yl)methanone;
(4-(1H-imidazol-2-yl)piperidin-1-yl)(4-(1H-indol-4-yl)phenyl)methanone;
(4-(1H-imidazol-2-yl)piperidin-1-yl)(4-(1H-indol-1-yl)phenyl)methanone;
(4-(1H-imidazol-2-yl)piperidin-1-yl)(3'-(trifluoromethyl)-[1,1'-biphenyl]-4-yl)methanone;
(4-(1H-imidazol-2-yl)piperidin-1-yl)(4-(benzo[d][1,3]dioxol-4-yl)phenyl)methanone;
(4-(1H-imidazol-2-yl)piperidin-1-yl)(1-phenyl-1H-indol-5-yl)methanone;
(4-(1H-imidazol-2-yl)piperidin-1-yl)(4-(5-(trifluoromethyl)thiophen-2-yl)phenyl)methanone;
(4-(1H-imidazol-2-yl)piperidin-1-yl)(4-(1H-indol-3-yl)phenyl)methanone;
(4-(1H-imidazol-2-yl)piperidin-1-yl)(4-(1H-indazol-3-yl)phenyl)methanone;
(4-((1H-imidazol-2-yl)methyl)piperidin-1-yl)(4'-(difluoromethyl)-[1,1'-biphenyl]-4-yl)methanone;
(4-(4-methyl-1H-imidazol-2-yl)piperidin-1-yl)(4-(2-methyl-1H-indol-3-yl)phenyl)methanone;
(4-(1H-indol-6-yl)phenyl)(4-(5-methyl-1H-imidazol-2-yl)piperidin-1-yl)methanone;
(4-(1H-imidazol-2-yl)piperidin-1-yl)(1H,1'H-[3,4'-biindol]-6-yl)methanone;
[4-(1H-imidazol-2-yl)-1-piperidyl]-[3-(1H-indol-3-yl)-1H-indol-6-yl]methanone;
(4-(1H-imidazol-2-yl)piperidin-1-yl)(4-(1H-indol-2-yl)phenyl)methanone;
(4-(5-methyl-1H-imidazol-2-yl)piperidin-1-yl)(3-phenyl-1H-indol-6-yl)methanone;
(4-(1H-imidazol-2-yl)piperidin-1-yl)(3-phenyl-1H-indol-6-yl)methanone;
(4-((1H-imidazol-2-yl)amino)piperidin-1-yl)(4'-(difluoromethyl)-[1,1'-biphenyl]-4-yl)methanone; and
(4-(5-fluoro-1H-indol-3-yl)phenyl)(4-(4-methyl-1H-imidazol-2-yl)piperidin-1-yl)methanone; and veterinary acceptable salts thereof. In yet another aspect, the composition further comprises at least one veterinary acceptable excipient. In another aspect, the composition is administered orally or by parenteral injection. In another aspect, the composition is administered orally. In yet another aspect, the composition is administered by subcutaneous injection or intramuscular injection. In another aspect, the composition is administered at least once daily. In yet another aspect, the composition is administered once daily. In yet another aspect, the composition is administered orally, once daily.

In one aspect of the invention, is a composition comprising a compound selected from the group consisting of:
(4-((1H-imidazol-2-yl)amino)piperidin-1-yl)(4'-fluoro-[1,1'-biphenyl]-4-yl)methanone;
(4-(1H-imidazol-2-yl)piperidin-1-yl)(4'-(trifluoromethyl)-[1,1'-biphenyl]-4-yl)methanone;
(4-(5-methyl-1H-imidazol-2-yl)piperidin-1-yl)(4'-(trifluoromethyl)-[1,1'-biphenyl]-4-yl)methanone;
(4-(1H-indol-3-yl)phenyl)(4-(5-methyl-1H-imidazol-2-yl)piperidin-1-yl)methanone;

(4-(1H-indazol-3-yl)phenyl)(4-(5-methyl-1H-imidazol-2-yl)piperidin-1-yl)methanone;

(4-(1H-imidazol-2-yl)piperidin-1-yl)(4'-(difluoromethyl)-[1,1'-biphenyl]-4-yl)methanone;

(4-(1H-imidazol-2-yl)piperidin-1-yl)(4-(benzo[d][1,3]dioxol-4-yl)phenyl)methanone;

(4-(1H-imidazol-2-yl)piperidin-1-yl)(4-(1H-indol-3-yl)phenyl)methanone;

(4-((1H-imidazol-2-yl)methyl)piperidin-1-yl)(4'-(difluoromethyl)-[1,1'-biphenyl]-4-yl)methanone; and (4-(4-methyl-1H-imidazol-2-yl)piperidin-1-yl)(4-(2-methyl-1H-indol-3-yl)phenyl)methanone; and veterinary acceptable salts thereof. In yet another aspect, the composition further comprises at least one veterinary acceptable excipient. In another aspect, the composition is administered orally or by parenteral injection. In another aspect, the composition is administered orally. In yet another aspect, the composition is administered by subcutaneous injection or intramuscular injection. In another aspect, the composition is administered at least once daily. In yet another aspect, the composition is administered once daily. In yet another aspect, the composition is administered orally, once daily.

In one aspect of the invention, is a composition comprising a compound selected from the group consisting of:

(4-((1H-imidazol-2-yl)amino)piperidin-1-yl)(4'-fluoro-[1,1'-biphenyl]-4-yl)methanone;

(4-(1H-indol-3-yl)phenyl)(4-(5-methyl-1H-imidazol-2-yl)piperidin-1-yl)methanone;

(4-(1H-indazol-3-yl)phenyl)(4-(5-methyl-1H-imidazol-2-yl)piperidin-1-yl)methanone;

(4-(1H-imidazol-2-yl)piperidin-1-yl)(4'-(difluoromethyl)-[1,1'-biphenyl]-4-yl)methanone;

(4-(1H-imidazol-2-yl)piperidin-1-yl)(4-(benzo[d][1,3]dioxol-4-yl)phenyl)methanone; and (4-((1H-imidazol-2-yl)methyl)piperidin-1-yl)(4'-(difluoromethyl)-[1,1'-biphenyl]-4-yl)methanone; and veterinary acceptable salts thereof. In another aspect, the composition further comprises at least one veterinary acceptable excipient. In another aspect, the composition is administered orally or by parenteral injection. In another aspect, the composition is administered orally. In yet another aspect, the composition is administered by subcutaneous injection or intramuscular injection. In another aspect, the composition is administered at least once daily. In yet another aspect, the composition is administered once daily. In yet another aspect, the composition is administered orally, once daily.

In one aspect of the invention, is a composition comprising a compound selected from the group consisting of:

(4-(1H-indol-3-yl)phenyl)(4-(5-methyl-1H-imidazol-2-yl)piperidin-1-yl)methanone;

(4-(1H-indazol-3-yl)phenyl)(4-(5-methyl-1H-imidazol-2-yl)piperidin-1-yl)methanone;

(4-(1H-imidazol-2-yl)piperidin-1-yl)(4'-(difluoromethyl)-[1,1'-biphenyl]-4-yl)methanone; and (4-((1H-imidazol-2-yl)methyl)piperidin-1-yl)(4'-(difluoromethyl)-[1,1'-biphenyl]-4-yl)methanone; and veterinary acceptable salts thereof. In yet another aspect, the composition further comprises at least one veterinary acceptable excipient. In another aspect, the composition is administered orally or by parenteral injection. In another aspect, the composition is administered orally. In yet another aspect, the composition is administered by subcutaneous injection or intramuscular injection. In another aspect, the composition is administered at least once daily. In yet another aspect, the composition is administered once daily. In yet another aspect, the composition is administered orally, once daily.

In one aspect of the invention, is a composition comprising a compound selected from (4-(1H-indol-3-yl)phenyl)(4-(5-methyl-1H-imidazol-2-yl)piperidin-1-yl)methanone or 4-(1H-imidazol-2-yl)piperidin-1-yl)(4'-(difluoromethyl)-[1,1'-biphenyl]-4-yl)methanone; and veterinary acceptable salts thereof. In another aspect, the composition further comprises at least one veterinary acceptable excipient. In another aspect, the composition is administered orally or by parenteral injection. In another aspect, the composition is administered orally. In yet another aspect, the composition is administered by subcutaneous injection or intramuscular injection. In another aspect, the composition is administered at least once daily. In yet another aspect, the composition is administered once daily. In yet another aspect, the composition is administered orally, once daily.

In one aspect of the invention, is a composition comprising the compound, (4-(1H-indol-3-yl)phenyl)(4-(5-methyl-1H-imidazol-2-yl)piperidin-1-yl)methanone; and veterinary acceptable salts thereof. In another aspect, the composition further comprises at least one veterinary acceptable excipient. In another aspect, the composition is administered orally or by parenteral injection. In another aspect, the composition is administered orally. In yet another aspect, the composition is administered by subcutaneous injection or intramuscular injection. In another aspect, the composition is administered at least once daily. In yet another aspect, the composition is administered once daily. In yet another aspect, the composition is administered orally, once daily.

In another aspect of the invention is a composition comprising the compound, 4-(1H-imidazol-2-yl)piperidin-1-yl)(4'-(difluoromethyl)-[1,1'-biphenyl]-4-yl)methanone; and veterinary acceptable salts thereof. In another aspect, the composition further comprises at least one veterinary acceptable excipient. In another aspect, the composition is administered orally or by parenteral injection. In another aspect, the composition is administered orally. In yet another aspect, the composition is administered by subcutaneous injection or intramuscular injection. In another aspect, the composition is administered at least once daily. In yet another aspect, the composition is administered once daily. In yet another aspect, the composition is administered orally, once daily.

In yet another aspect of the invention, is a method of treating an animal with MMVD, CHF and/or asymptomatic heart failure, by administering a therapeutic amount of a compound to the animal in need thereof, wherein the compound is selected from the group consisting of:

(4-((1H-imidazol-2-yl)amino)piperidin-1-yl)(4'-fluoro-[1,1'-biphenyl]-4-yl)methanone;

(4-(1H-imidazol-2-yl)piperidin-1-yl)(3'-(methylsulfonyl)-[1,1'-biphenyl]-4-yl)methanone;

(4-(1H-imidazol-2-yl)piperidin-1-yl)(4'-(trifluoromethyl)-[1,1'-biphenyl]-4-yl)methanone;

(4-(5-methyl-1H-imidazol-2-yl)piperidin-1-yl)(4'-(trifluoromethyl)-[1,1'-biphenyl]-4-yl)methanone;

(4-(1H-indol-3-yl)phenyl)(4-(5-methyl-1H-imidazol-2-yl)piperidin-1-yl)methanone;

(4-(1H-indazol-3-yl)phenyl)(4-(5-methyl-1H-imidazol-2-yl)piperidin-1-yl)methanone;

(4-((1H-imidazol-2-yl)amino)piperidin-1-yl)(4'-(trifluoromethyl)-[1,1'-biphenyl]-4-yl)methanone;

(4-(1H-imidazol-2-yl)piperidin-1-yl)(4-phenoxyphenyl)methanone;

(4-(1H-imidazol-2-yl)piperidin-1-yl)(4-(phenylamino)phenyl)methanone;

(4-(1H-imidazol-2-yl)piperidin-1-yl)(3'-chloro-[1,1'-biphenyl]-4-yl)methanone,
trifluoroacetic acid salt;
(4-(1H-imidazol-2-yl)piperidin-1-yl)(6-phenylpyridin-3-yl) methanone, trifluoroacetic acid salt;
(4-((1H-imidazol-2-yl)methyl)piperidin-1-yl)(4'-(trifluoromethyl)-[1,1'-biphenyl]-4-yl)methanone, trifluoroacetic acid salt;
(4-(1H-imidazol-2-yl)piperidin-1-yl)(4-(benzo[d][1,3]dioxol-5-yl)phenyl)methanone,
trifluoroacetic acid salt;
(4-(1H-imidazol-2-yl)piperidin-1-yl)(9H-carbazol-2-yl) methanone;
(4-(1H-imidazol-2-yl)piperidin-1-yl)(dibenzo[b,d]furan-3-yl)methanone, trifluoroacetic acid salt;
(4-(1H-imidazol-2-yl)piperidin-1-yl)(4'-(difluoromethyl)-[1,1'-biphenyl]-4-yl)methanone;
(4-(1H-imidazol-2-yl)piperidin-1-yl)(4-(1H-indol-4-yl)phenyl)methanone;
(4-(1H-imidazol-2-yl)piperidin-1-yl)(4-(1H-indol-1-yl)phenyl)methanone;
(4-(1H-imidazol-2-yl)piperidin-1-yl)(3'-(trifluoromethyl)-[1,1'-biphenyl]-4-yl)methanone;
(4-(1H-imidazol-2-yl)piperidin-1-yl)(4-(benzo[d][1,3]dioxol-4-yl)phenyl)methanone;
(4-(1H-imidazol-2-yl)piperidin-1-yl)(1-phenyl-1H-indol-5-yl)methanone;
(4-(1H-imidazol-2-yl)piperidin-1-yl)(4-(5-(trifluoromethyl) thiophen-2-yl)phenyl)methanone;
(4-(1H-imidazol-2-yl)piperidin-1-yl)(4-(1H-indol-3-yl)phenyl)methanone;
(4-(1H-imidazol-2-yl)piperidin-1-yl)(4-(1H-indazol-3-yl) phenyl)methanone;
(4-((1H-imidazol-2-yl)methyl)piperidin-1-yl)(4'-(difluoromethyl)-[1,1'-biphenyl]-4-yl)methanone;
(4-(4-methyl-1H-imidazol-2-yl)piperidin-1-yl)(4-(2-methyl-1H-indol-3-yl)phenyl)methanone;
(4-(1H-indol-6-yl)phenyl)(4-(5-methyl-1H-imidazol-2-yl) piperidin-1-yl)methanone;
(4-(1H-imidazol-2-yl)piperidin-1-yl)(1H,1'H-[3,4'-biindol]-6-yl)methanone;
[4-(1H-imidazol-2-yl)-1-piperidyl]-[3-(1H-indol-3-yl)-1H-indol-6-yl]methanone;
(4-(1H-imidazol-2-yl)piperidin-1-yl)(4-(1H-indol-2-yl)phenyl)methanone;
(4-(5-methyl-1H-imidazol-2-yl)piperidin-1-yl)(3-phenyl-1H-indol-6-yl)methanone;
(4-(1H-imidazol-2-yl)piperidin-1-yl)(3-phenyl-1H-indol-6-yl)methanone;
(4-((1H-imidazol-2-yl)amino)piperidin-1-yl)(4'-(difluoromethyl)-[1,1'-biphenyl]-4-yl)methanone; and
(4-(5-fluoro-1H-indol-3-yl)phenyl)(4-(4-methyl-1H-imidazol-2-yl)piperidin-1-yl)methanone; and veterinary acceptable salts thereof. In yet another aspect, the animal is a companion animal. In another aspect, the companion animal is canine.

In yet another aspect of the invention, is a method of treating an animal with MMVD, CHF and/or asymptomatic heart failure, by administering a therapeutic amount of a compound to the animal in need thereof, wherein the compound is selected from the group consisting of:
(4-((1H-imidazol-2-yl)amino)piperidin-1-yl)(4'-fluoro-[1,1'-biphenyl]-4-yl)methanone;
(4-(1H-imidazol-2-yl)piperidin-1-yl)(4'-(trifluoromethyl)-[1,1'-biphenyl]-4-yl)methanone;
(4-(5-methyl-1H-imidazol-2-yl)piperidin-1-yl)(4'-(trifluoromethyl)-[1,1'-biphenyl]-4-yl)methanone;
(4-(1H-indol-3-yl)phenyl)(4-(5-methyl-1H-imidazol-2-yl) piperidin-1-yl)methanone;
(4-(1H-indazol-3-yl)phenyl)(4-(5-methyl-1H-imidazol-2-yl)piperidin-1-yl)methanone;
(4-(1H-imidazol-2-yl)piperidin-1-yl)(4'-(difluoromethyl)-[1,1'-biphenyl]-4-yl)methanone;
(4-(1H-imidazol-2-yl)piperidin-1-yl)(4-(benzo[d][1,3]dioxol-4-yl)phenyl)methanone;
(4-(1H-imidazol-2-yl)piperidin-1-yl)(4-(1H-indol-3-yl)phenyl)methanone;
(4-((1H-imidazol-2-yl)methyl)piperidin-1-yl)(4'-(difluoromethyl)-[1,1'-biphenyl]-4-yl)methanone; and
(4-(4-methyl-1H-imidazol-2-yl)piperidin-1-yl)(4-(2-methyl-1H-indol-3-yl)phenyl)methanone; and veterinary acceptable salts thereof. In yet another aspect, the animal is a companion animal, preferably canine.

In yet another aspect of the invention, is a method of treating an animal with MMVD, CHF and/or asymptomatic heart failure, by administering a therapeutic amount of a compound to the animal in need thereof, wherein the compound is selected from the group consisting of:
(4-((1H-imidazol-2-yl)amino)piperidin-1-yl)(4'-fluoro-[1,1'-biphenyl]-4-yl)methanone;
(4-(1H-indol-3-yl)phenyl)(4-(5-methyl-1H-imidazol-2-yl) piperidin-1-yl)methanone;
(4-(1H-indazol-3-yl)phenyl)(4-(5-methyl-1H-imidazol-2-yl)piperidin-1-yl)methanone;
(4-(1H-imidazol-2-yl)piperidin-1-yl)(4'-(difluoromethyl)-[1,1'-biphenyl]-4-yl)methanone;
(4-(1H-imidazol-2-yl)piperidin-1-yl)(4-(benzo[d][1,3]dioxol-4-yl)phenyl)methanone; and
(4-((1H-imidazol-2-yl)methyl)piperidin-1-yl)(4'-(difluoromethyl)-[1,1'-biphenyl]-4-yl)methanone; and veterinary acceptable salts thereof. In another aspect, the animal is a companion animal. In another aspect, the companion animal is canine.

In yet another aspect of the invention, is a method of treating an animal with MMVD, CHF and/or asymptomatic heart failure, by administering a therapeutic amount of a compound to the animal in need thereof, wherein the compound is selected from the group consisting of:
(4-(1H-indol-3-yl)phenyl)(4-(5-methyl-1H-imidazol-2-yl) piperidin-1-yl)methanone;
(4-(1H-indazol-3-yl)phenyl)(4-(5-methyl-1H-imidazol-2-yl)piperidin-1-yl)methanone;
(4-(1H-imidazol-2-yl)piperidin-1-yl)(4'-(difluoromethyl)-[1,1'-biphenyl]-4-yl)methanone;
and (4-((1H-imidazol-2-yl)methyl)piperidin-1-yl)(4'-(difluoromethyl)-[1,1'-biphenyl]-4-yl)methanone; and veterinary acceptable salts thereof. In yet another aspect, the animal is a companion animal. In another aspect, the companion animal is canine.

In yet another aspect of the invention, is a method of treating an animal with MMVD, CHF and/or asymptomatic heart failure, by administering a therapeutic amount of a compound to the animal in need thereof, wherein the compound is (4-(1H-indol-3-yl)phenyl)(4-(5-methyl-1H-imidazol-2-yl)piperidin-1-yl)methanone or 4-(1H-imidazol-2-yl) piperidin-1-yl)(4'-(difluoromethyl)-[1,1'-biphenyl]-4-yl) methanone; and veterinary acceptable salts thereof. In another aspect, the animal is a companion animal. In another aspect, the companion animal is canine.

In yet another aspect of the invention, is a method of treating an animal with MMVD, CHF and/or asymptomatic heart failure, by administering a therapeutic amount of (4-(1H-indol-3-yl)phenyl)(4-(5-methyl-1H-imidazol-2-yl) piperidin-1-yl)methanone; and veterinary acceptable salts thereof to the animal in need thereof. In another aspect, the animal is a companion animal. In another aspect the companion animal is canine.

In yet another aspect of the invention, is a method of treating an animal with MMVD, CHF and/or asymptomatic heart failure, by administering a therapeutic amount of 4-(1H-imidazol-2-yl)piperidin-1-yl)(4'-(difluoromethyl)-[1,1'-biphenyl]-4-yl)methanone; and veterinary acceptable salts thereof, to the animal in need thereof. In another aspect, the animal is a companion animal. In yet another aspect, the companion animal is canine.

In yet another aspect of the invention, is the use of a compound selected from the group consisting of:

(4-((1H-imidazol-2-yl)amino)piperidin-1-yl)(4'-fluoro-[1,1'-biphenyl]-4-yl)methanone;

(4-(1H-imidazol-2-yl)piperidin-1-yl)(3'-(methylsulfonyl)-[1,1'-biphenyl]-4-yl)methanone;

(4-(1H-imidazol-2-yl)piperidin-1-yl)(4'-(trifluoromethyl)-[1,1'-biphenyl]-4-yl)methanone;

(4-(5-methyl-1H-imidazol-2-yl)piperidin-1-yl)(4'-(trifluoromethyl)-[1,1'-biphenyl]-4-yl)methanone;

(4-(1H-indol-3-yl)phenyl)(4-(5-methyl-1H-imidazol-2-yl)piperidin-1-yl)methanone;

(4-(1H-indazol-3-yl)phenyl)(4-(5-methyl-1H-imidazol-2-yl)piperidin-1-yl)methanone;

(4-((1H-imidazol-2-yl)amino)piperidin-1-yl)(4'-(trifluoromethyl)-[1,1'-biphenyl]-4-yl)methanone;

(4-(1H-imidazol-2-yl)piperidin-1-yl)(4-phenoxyphenyl)methanone;

(4-(1H-imidazol-2-yl)piperidin-1-yl)(4-(phenylamino)phenyl)methanone;

(4-(1H-imidazol-2-yl)piperidin-1-yl)(3'-chloro-[1,1'-biphenyl]-4-yl)methanone, trifluoroacetic acid salt;

(4-(1H-imidazol-2-yl)piperidin-1-yl)(6-phenylpyridin-3-yl)methanone, trifluoroacetic acid salt;

(4-((1H-imidazol-2-yl)methyl)piperidin-1-yl)(4'-(trifluoromethyl)-[1,1'-biphenyl]-4-yl)methanone, trifluoroacetic acid salt;

(4-(1H-imidazol-2-yl)piperidin-1-yl)(4-(benzo[d][1,3]dioxol-5-yl)phenyl)methanone, trifluoroacetic acid salt;

(4-(1H-imidazol-2-yl)piperidin-1-yl)(9H-carbazol-2-yl)methanone;

(4-(1H-imidazol-2-yl)piperidin-1-yl)(dibenzo[b,d]furan-3-yl)methanone, trifluoroacetic acid salt;

(4-(1H-imidazol-2-yl)piperidin-1-yl)(4'-(difluoromethyl)-[1,1'-biphenyl]-4-yl)methanone;

(4-(1H-imidazol-2-yl)piperidin-1-yl)(4-(1H-indol-4-yl)phenyl)methanone;

(4-(1H-imidazol-2-yl)piperidin-1-yl)(4-(1H-indol-1-yl)phenyl)methanone;

(4-(1H-imidazol-2-yl)piperidin-1-yl)(3'-(trifluoromethyl)-[1,1'-biphenyl]-4-yl)methanone;

(4-(1H-imidazol-2-yl)piperidin-1-yl)(4-(benzo[d][1,3]dioxol-4-yl)phenyl)methanone;

(4-(1H-imidazol-2-yl)piperidin-1-yl)(1-phenyl-1H-indol-5-yl)methanone;

(4-(1H-imidazol-2-yl)piperidin-1-yl)(4-(5-(trifluoromethyl)thiophen-2-yl)phenyl)methanone;

(4-(1H-imidazol-2-yl)piperidin-1-yl)(4-(1H-indol-3-yl)phenyl)methanone;

(4-(1H-imidazol-2-yl)piperidin-1-yl)(4-(1H-indazol-3-yl)phenyl)methanone;

(4-((1H-imidazol-2-yl)methyl)piperidin-1-yl)(4'-(difluoromethyl)-[1,1'-biphenyl]-4-yl)methanone;

(4-(4-methyl-1H-imidazol-2-yl)piperidin-1-yl)(4-(2-methyl-1H-indol-3-yl)phenyl)methanone;

(4-(1H-indol-6-yl)phenyl)(4-(5-methyl-1H-imidazol-2-yl)piperidin-1-yl)methanone;

(4-(1H-imidazol-2-yl)piperidin-1-yl)(1H,1'H-[3,4'-biindol]-6-yl)methanone;

[4-(1H-imidazol-2-yl)-1-piperidyl]-[3-(1H-indol-3-yl)-1H-indol-6-yl]methanone;

(4-(1H-imidazol-2-yl)piperidin-1-yl)(4-(1H-indol-2-yl)phenyl)methanone;

(4-(5-methyl-1H-imidazol-2-yl)piperidin-1-yl)(3-phenyl-1H-indol-6-yl)methanone;

(4-(1H-imidazol-2-yl)piperidin-1-yl)(3-phenyl-1H-indol-6-yl)methanone;

(4-((1H-imidazol-2-yl)amino)piperidin-1-yl)(4'-(difluoromethyl)-[1,1'-biphenyl]-4-yl)methanone; and (4-(5-fluoro-1H-indol-3-yl)phenyl)(4-(4-methyl-1H-imidazol-2-yl)piperidin-1-yl)methanone; and veterinary acceptable salts thereof, to prepare a medicament for treating an animal with MMVD, CHF and/or asymptomatic heart failure. In another aspect, animal is a companion animal. In another aspect, the companion animal is canine.

In another aspect of the invention, is the use of a compound selected from the group consisting of:

(4-((1H-imidazol-2-yl)amino)piperidin-1-yl)(4'-fluoro-[1,1'-biphenyl]-4-yl)methanone;

(4-(1H-imidazol-2-yl)piperidin-1-yl)(4'-(trifluoromethyl)-[1,1'-biphenyl]-4-yl)methanone;

(4-(5-methyl-1H-imidazol-2-yl)piperidin-1-yl)(4'-(trifluoromethyl)-[1,1'-biphenyl]-4-yl)methanone;

(4-(1H-indol-3-yl)phenyl)(4-(5-methyl-1H-imidazol-2-yl)piperidin-1-yl)methanone;

(4-(1H-indazol-3-yl)phenyl)(4-(5-methyl-1H-imidazol-2-yl)piperidin-1-yl)methanone;

(4-(1H-imidazol-2-yl)piperidin-1-yl)(4'-(difluoromethyl)-[1,1'-biphenyl]-4-yl)methanone;

(4-(1H-imidazol-2-yl)piperidin-1-yl)(4-(benzo[d][1,3]dioxol-4-yl)phenyl)methanone;

(4-(1H-imidazol-2-yl)piperidin-1-yl)(4-(1H-indol-3-yl)phenyl)methanone;

(4-((1H-imidazol-2-yl)methyl)piperidin-1-yl)(4'-(difluoromethyl)-[1,1'-biphenyl]-4-yl)methanone; and (4-(4-methyl-1H-imidazol-2-yl)piperidin-1-yl)(4-(2-methyl-1H-indol-3-yl)phenyl)methanone; and veterinary acceptable salts thereof, to prepare a medicament for treating an animal with MMVD, CHF and/or asymptomatic heart failure. In another aspect, animal is a companion animal. In another aspect, the companion animal is canine.

In another aspect of the invention, is the use of a compound selected from the group consisting of:

(4-((1H-imidazol-2-yl)amino)piperidin-1-yl)(4'-fluoro-[1,1'-biphenyl]-4-yl)methanone;

(4-(1H-indol-3-yl)phenyl)(4-(5-methyl-1H-imidazol-2-yl)piperidin-1-yl)methanone;

(4-(1H-indazol-3-yl)phenyl)(4-(5-methyl-1H-imidazol-2-yl)piperidin-1-yl)methanone;

(4-(1H-imidazol-2-yl)piperidin-1-yl)(4'-(difluoromethyl)-[1,1'-biphenyl]-4-yl)methanone;

(4-(1H-imidazol-2-yl)piperidin-1-yl)(4-(benzo[d][1,3]dioxol-4-yl)phenyl)methanone; and (4-((1H-imidazol-2-yl)methyl)piperidin-1-yl)(4'-(difluoromethyl)-[1,1'-biphenyl]-4-yl)methanone; and veterinary acceptable salts thereof, to prepare a medicament for treating an animal with MMVD, CHF and/or asymptomatic heart failure. In another aspect, animal is a companion animal. In another aspect, the companion animal is canine.

In one aspect of the invention, is the use of a compound selected from the group consisting of:

(4-(1H-indol-3-yl)phenyl)(4-(5-methyl-1H-imidazol-2-yl) piperidin-1-yl)methanone;

(4-(1H-indazol-3-yl)phenyl)(4-(5-methyl-1H-imidazol-2-yl)piperidin-1-yl)methanone;

(4-(1H-imidazol-2-yl)piperidin-1-yl)(4'-(difluoromethyl)-[1,1'-biphenyl]-4-yl)methanone;

and (4-((1H-imidazol-2-yl)methyl)piperidin-1-yl)(4'-(difluoromethyl)-[1,1'-biphenyl]-4-yl)methanone; and veterinary acceptable salts thereof, to prepare a medicament for treating an animal with MMVD, CHF and/or asymptomatic heart failure. In another aspect, animal is a companion animal. In another aspect, the companion animal is canine.

In one aspect of the invention, is the use of a compound selected from (4-(1H-indol-3-yl)phenyl)(4-(5-methyl-1H-imidazol-2-yl)piperidin-1-yl)methanone or 4-(1H-imidazol-2-yl)piperidin-1-yl)(4'-(difluoromethyl)-[1,1'-biphenyl]-4-yl)methanone; and veterinary acceptable salts thereof, to prepare a medicament for treating an animal with MMVD, CHF and/or asymptomatic heart failure. In another aspect, animal is a companion animal. In another aspect, the companion animal is canine.

In one aspect of the invention, is the use of the compound, (4-(1H-indol-3-yl)phenyl)(4-(5-methyl-1H-imidazol-2-yl) piperidin-1-yl)methanone; and veterinary acceptable salts thereof, to prepare a medicament for treating an animal with MMVD, CHF and/or asymptomatic heart failure. In another aspect, animal is a companion animal. In another aspect, the companion animal is canine.

In another aspect of the invention is the use of the compound, 4-(1H-imidazol-2-yl)piperidin-1-yl)(4'-(difluoromethyl)-[1,1'-biphenyl]-4-yl)methanone; and veterinary acceptable salts thereof, to prepare a medicament for treating an animal with MMVD, CHF and/or asymptomatic heart failure. In another aspect, animal is a companion animal. In another aspect, the companion animal is canine.

In yet another aspect of the invention is the treatment of MMVD, CHF and/or asymptomatic heart failure, in an animal by administering a therapeutically effective amount of a compound of the invention in combination with at least one additional cardiovascular agent to the animal in need thereof. In another aspect of the invention, the at least one additional cardiovascular agent is selected from the group consisting of: an ACE inhibitor, a diuretic, and a spironolactone. In another aspect, the ACE inhibitor is enalapril, captopril, or ramipril.

DESCRIPTION OF THE INVENTION

Definitions

For purposes of the invention, as described and claimed herein, the following terms and phrases are defined as follows:

"Additional veterinary (or pharmaceutical) agent(s)" as used herein, unless otherwise indicated, refers to other veterinary or pharmaceutical compounds or products (i.e., drugs) that provide a therapeutically effective amount of said agent(s) that are useful for the treatment of MMVD, CHF, and/or asymptomatic heart failure in an animal, preferably canine.

"Animal(s)", as used herein, unless otherwise indicated, refers to an individual animal that is a mammal. Specifically, mammal refers to a vertebrate animal that is human and non-human, which are members of the taxonomic class Mammalia. Non-exclusive examples of non-human mammals include companion animals. Non-exclusive examples of a companion animal include: dog, cat, and horse. The preferred companion animal is canine.

"Asymptomatic (occult, preclinical) heart failure" as used herein, unless otherwise indicated, refers to any contractile disorder or disease of the heart which is due to MMVD.

"Compounds of the invention", unless otherwise indicated, refers to the 5-HT2B antagonist non-comparator compounds described herein; (i.e., Examples 1-34).

"Congestive heart failure", or "heart failure" unless otherwise indicated, refers to a manifested process wherein the heart is unable to keep up with the demands of blood supply to the body and generally results in fluid buildup in the lungs resulting from increased cardiac and pulmonary pressures. The term(s) also relate to any contractile disorder or disease of the heart. Clinical manifestations are as a rule the result of changes to the heart's cellular and molecular components and to mediators that drive homeostatic control that leads to an increase in heart size and deterioration of cardiac function.

"Myxomatous mitral valve degeneration (MMVD)", unless otherwise indicated, refers to the manifested process of mitral valve degeneration. MMVD is generally detected as a heart murmur by auscultation. MMVD also includes synonymous medicinal terms: mitral valve disease (MVD); degenerative mitral valve disease (DMVD); chronic valve disease (CVD); chronic valvular heart disease (CVHD); and atrial ventricular valvular insufficiency (AVVI).

"Therapeutically effective amount", unless otherwise indicated, refers to an amount of a compound of the invention that (i) treat MMVD, CHF, and/or asymptomatic heart failure in an animal (ii) attenuates, ameliorates, or eliminates one or more symptoms of MMVD, CHF, and/or asymptomatic heart failure in an animal, or (iii) prevents or delays the onset of MMVD, CHF, and/or asymptomatic heart failure in an animal.

"Treatment", "treating", "treat", and the like, as used herein, unless otherwise indicated, refers to alleviating, halting, or slowing the progression of MMVD, CHF, and/or asymptomatic heart failure in an animal. As used herein, these terms also encompass, depending on the condition of the animal, preventing the onset of a disorder or condition, or of symptoms associated with a disorder or condition, including reducing the severity of a disorder or condition or symptoms associated therewith. Thus, treatment can refer to administration of a compound of the invention to an animal that is not at the time of administration diagnosed with CHF.

"Veterinary acceptable", unless otherwise indicated, refers to a substance or composition that is compatible chemically and/or toxicologically with the animal receiving said substance or composition. The term also contemplates "pharmaceutical or pharmaceutically" acceptable.

Myxomatous mitral valve degeneration (MMVD) is the most common acquired type of heart disease and new heart murmurs in older dogs. A heart murmur is a sound heard with every heartbeat and is caused by turbulent blood flow in the heart. MMVD is a manifestation of a process that can affect the mitral valve. MMVD affects primarily small breed dogs later in life but can affect larger breed dogs. Some smaller breed dogs are affected earlier in life than others with the Cavalier King Charles Spaniel being the most prominent breed described to date.

The mitral valve is the valve between the left atrium and the left ventricle. Oxygenated blood from the lungs enters the left atrium, passes through the mitral valve into the left ventricle and subsequently pumped to the body. The mitral valve closes when the left ventricle contracts which prevents blood from flowing back into the left atrium. A healthy mitral valve is thin and supple and is anchored in place by chordae tendonae (CT). Myxomatous degeneration is a process that occurs when the valve becomes thickened with formation of small nodules which prevent complete closing of the valves allowing back flow (mitral regurgitation) of blood into the left atrium. Over time, the atrium and ventricles compensate by enlarging and the leak progressively worsens. As leaking volume increases, atrial pressure increases. In some instances, CT may rupture causing a partially unanchored mitral valve (mitral valve pro-lapse). The increase in pressure is transmitted to the lungs leading to CHF.

A heart murmur is generally the earliest means by which MMVD can be detected. After the murmur is detected, MMVD symptoms may not appear for three to four years. Often the first outward sign of worsening MMVD is a cough or increased respiratory effort which may be due to airway pressure from the enlarged heart and/or fluid congestion in the lungs and heart.

There are no medications that are proven to slow or prevent the progression of MMVD, particularly in the early stages of the disease. Treatments are administered to manage MMVD, CHF, and/or asymptomatic heart failure, including: furosemide, pimobendan, an ACE inhibitor (e.g., enalapril) and spironolactone. Furosemide is a potent diuretic and removes water from the body thereby decreasing pulmonary fluid congestion. Pimobendan helps the heart work more effectively, aids in decreasing cardiac remodeling and has been shown to improve survival in MMVD patients. ACE inhibitors and spironolactone block deleterious compensatory mechanisms that occur with severe heart disease and have been shown to prolong survival as well. Side effects of these drugs include allergic reaction, staggering, loss of appetite, lethargy, diarrhea, and fainting. Other medications that are sometimes used in treatment of CHF include hydrochlorothiazide, amlodipine, torsemide, and digoxin.

Despite development of new drugs and treatment regimens, uncertainty remains about when to treat and what the best interventions are for some of these animals. In 2009, an objective classification system was developed to categorize heart disease that is based on risk factors and clinical and diagnostic imaging signs.

Heart failure is divided in different stages, which were defined by different classification systems, e.g. the International Small Animal Cardiac Health Council (ISACHC), the New York Heart Association (NYHA) functional classification systems and the currently used classification according to the Consensus Statements of the American College of Veterinary Internal Medicine (ACVIM), 2009. To remove any ambiguity between classification systems, the classification systems described below are to be considered synonymous.

Classification according to the International Small Animal Cardiac Health Council (ISACHC) System: Class I: asymptomatic (also known as occult or preclinical); Class IA: no evidence of compensation for underlying heart disease (no volume overload or pressure overload detected radiographically or echocardiographically); Class IB: clinical signs of compensation for underlying heart disease (volume overload or pressure overload detected radiographically or echocardiographically); Class II: mild to moderate heart failure with clinical signs at rest or with mild exercise (treatment required); Class III: advanced heart failure; clinical signs of severe congestive heart failure; Class IIIA: home treatment possible; and Class IIIB: requires hospitalization.

New York Heart Association (NYHA) functional classification system: Class I: describes patients with asymptomatic heart disease (e.g., chronic valvular heart disease (CVHD) is present, but no clinical signs are evident even with exercise); Class II: describes patients with heart disease that causes clinical signs only during strenuous exercise; Class III: describes patients with heart disease that causes clinical signs with routine daily activities or mild exercise; and Class IV: describes patients with heart disease that causes severe clinical signs even at rest.

The ACVIM system describes four basic stages of heart disease and failure: Stage A: patients at high risk for developing heart disease but that currently have no identifiable structural disorder of the heart; Stage B: patients with structural heart disease (e.g., the typical murmur of mitral valve regurgitation is present), but that have never developed clinical signs caused by heart failure (because of important clinical implications for prognosis and treatment, the panel further subdivided Stage B into Stage B1 and B2). Stage B1: asymptomatic patients that have no radiographic or echocardiographic evidence of cardiac remodeling in response to CVHD. Stage B2: asymptomatic patients that have hemodynamically significant valve regurgitation, as evidenced by radiographic or echocardiographic findings of left sided heart enlargement. Stage C: patients with past or current clinical signs of heart failure associated with structural heart disease. Stage D: patients with end-stage disease with clinical signs of heart failure caused by CVHD that are refractory to standard therapy.

The pathology of the heart begins with ISACHC Class I, NYHA Class I and ACVIM stage B2 in which cardiac murmur or cardiac chamber enlargement, but no clinical symptoms are present (ISACHC Class I or asymptomatic/occult/preclinical stage). Clinical symptoms become manifest in the course of progression of the disease (ISACHC Class II or III, NYHA class II, III or IV, ACVIM stage C and D).

Despite this information on categorizing heart disease severity, there has been little evidence to support the utility of medical intervention for animals with Stage B disease. However, in 2016, the results of a large prospective, randomized, placebo-controlled, blinded clinical trial to evaluate pimobendan (positive inotrope) treatment in dogs with Stage B2 disease were published. The EPIC trial (J. Vet Intern Med., 2016, November; 30(6), 1765-1779) was designed to assess whether or not treatment with pimobendan (0.2 or 0.3 mg/kg twice a day) would delay the onset of signs of left-sided congestive heart failure (CHF). Dogs must have had at least a grade 3/6 heart murmur with the point of maximal intensity over the mitral valve; have radiographic evidence of cardiomegaly defined as a VHS >10.5; have echocardiographic evidence of mitral valvular lesions and regurgitation as well as evidence of left atrial and left ventricular dilatation, defined as left atrial to aortic root ratio ≥1.6 and body weight normalized left ventricular internal diameter in diastole 1.7. Dogs were evaluated at one month and then every four months for the duration of the trial. Study results showed that dogs with Stage B2 MMVD treated with pimobendan took 462 days (15 months) longer to develop CHF or die from MMVD than dogs receiving placebo accounting for a 60% delay in prolonging their preclinical stage. This early intervention appears to prolong the time to onset of CHF.

Compounds of the invention have an affinity to 5-HT2B with minimal (if any) affinity to hERG. Therefore, the compounds of the invention may provide a potentially new drug to veterinarians for treating MMVD, CHF, and/or asymptomatic heart failure without the additional cardiac risk(s) associated with compounds that have an affinity to ERG.

Compounds of the invention may be synthesized by synthetic routes that include processes analogous to those well known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, "Reagents for Organic Synthesis", 1; 19, Wiley, New York (1967, 1999 ed.), or Beilsteins Handbuch der organischen Chemie, 4, Aufl. ed. Springer-Verlag, Berlin, including supplements (also available via the Beilstein online database)). For illustrative purposes, the reaction schemes depicted below demonstrate potential routes for synthesizing compounds of the invention, and key intermediates. A more detailed description of the individual reaction steps can be found in the Examples section. The skilled person will appreciate that the compounds of the invention could be made by methods other than those herein described by adaptation of the methods herein described and/or adaptation of methods known in the art, for example the art described herein, or using standard textbooks such as "Comprehensive Organic Transformations—A Guide to Functional Group Transformations", R C Larock, Wiley-VCH (1999 or later editions).

Schemes 1-7 outline the general procedures useful for the preparation and isolation of compounds of the invention. It is to be understood, however, that the invention, as fully described herein and as recited in the claims, is not intended to be limited by the details of the following schemes or modes of preparation.

In the Schemes and Examples below, the following reactants and miscellaneous abbreviations include: tetrahydrofuran (THF); dichloromethane (DCM); tert-butyl methyl ether (tBME); hydrochloric acid (HCl); trifluoroacetic acid (TFA); N, N-dimethylformamide (DMF); dimethylsulfoxide (DMSO); dimethoxymethane (DME); [dimethylamino(triazolo[4,5-b]pyridin-3-yloxy)methylidene]-dimethyl-azanium hexafluorophosphate (HATU); (dimethylamino)pyridine (DMAP); N,N-diisopropylcarbodiimide (DIC); N-ethyl-N'-(3-dimethylaminopropyl)carbodiimide hydrochloride (EdCl); tetramethyluronium hexafluorophosphate (HBTU); N,N-diisopropylethylamine (DIPEA); 1,8-diazabicyclo[5.4.0]undec-7-ene (DBU); 2-(1H-benzotriazole-1-yl)-1,1,3,3-tetramethyluronium tetrafluoroborate (TBTU); 2-(6-chloro-1-H-benzotriazole-1-yl)-1,1,3,3-tetramethylaminium hexafluorophosphate (HCTU); titanium(IV) isopropoxide ($Ti(O^iPr)_4$); aryl/heteroaryl (Ar/Het); (benzotriazol-1-yl-oxytripyrrolidinophosphonium hexafluorophosphate) (PyBOP); butyloxycarbonyl (BOC, protecting group); (1-cyano-2-ethoxy-2-oxoethylidenaminooxy)dimethyl-amino-morpholino-carbenium hexafluorophosphate (COMU); 1-propanephosphonic anhydride ($T_3P$); copper(I) iodide (CuI); copper(II) acetate ($Cu(OAC_2)$; palladium-tetrakis(triphenylphosphine) ($Pd(Ph_3P)_4$); sodium cyanoborohydride ($NaCNBH_3$); sodium bicarbonate ($NaHCO_3$); [1,1'-bis(diphenyl-phosphino)ferrocene]-dichloropalladium (II) complex with dichloromethane (1:1; $PdCl_2$(dppf)DCM); sodium carbonate ($Na_2CO_3$); tripotassium phosphate ($K_3PO_4$); potassium carbonate ($K_2CO_3$); lithium hydroxide (LiOH); Pd (palladium); thin layer chromatography (TLC); nuclear magnetic resonance (NMR); high pressure liquid chromatography (HPLC) and liquid chromatography mass spectrometry (LCMS).

In the Schemes below, the variables A, $A_1$, $A_2$, X, Ar, Het, $R_1$, $R_2$, $R_3$, and $R_4$ are defined as such: A=O or NH; $A_1$=C or N; $A_2$=bond or $CH_2$; X=F, Cl, Br, or I; $R_1$=H, F, Cl, —$CF_2$, —$CF_3$, —$OR_2$, —$NH_2$, —CN, —$SO_2CH_3$, —$SO_2CF_3$, a fused heterocyclic ring (e.g., indole, dioxarane); and —C(O)$NH_2$; $R_2$=alkyl; $R_3$ and $R_4$ are independently H or —$CH_3$; in addition, $R_3$ and $R_4$ can be joined to form a ring (i.e., a fused benzimidazole ring); Ar/Het refers to either Ar or Het; Ar refers to phenyl, substituted phenyl, substituted diphenyl, phenyl-indole, phenyl indazole, substituted diphenyl ether, carbazole, dibenzofuran, benzodioxole, indole, and substituted diphenylamine; Het refers to imidazole, thiazole, triazole, substituted thiophene, pyridyl-substituted phenyl, aminotriazole, thiadiazole, oxazole, and pyridine. "Alkyl", as used herein, refers to saturated monovalent hydrocarbon alkane radicals of the general formula $C_nH_{2n+1}$ (e.g., methyl, ethyl, propyl, isopropyl, sec-butyl, t-butyl, n-propyl, n-butyl, i-butyl, s-butyl, n-pentyl, 1-methylbutyl, 2-methylbutyl, 3-methylbutyl, and the like; and is further defined as having 1-8 carbon atoms (i.e., $C_1$-$C_8$).

Many of the compounds described herein were synthesized from commercially available carboxylic acids (e.g., 3 4'-(trifluoromethyl)-[1,1'-biphenyl]-4-carboxylic acid) and amines (4-(1H-imidazol-2-yl)piperidine hydrochloride salt). The compounds of the instant invention also include veterinary acceptable salts thereof.

The veterinary acceptable salts of compounds of the instant invention may also be prepared in a conventional manner. For example, a solution of a free base may be treated with the appropriate acid, either neat or in a suitable solvent, and the resulting salt isolated either by filtration or by evaporation under reduced pressure of the reaction solvent. For a review on suitable salts, see "Handbook of Pharmaceutical Salts: Properties, Selection, and Use" by Stahl and Wermuth (Wiley-VCH, Weinheim, Germany, 2002).

The compound of the invention may be used in its native form or as a salt. In cases where forming a stable nontoxic acid or base salt is desired, administration of the compound as a veterinary acceptable salt may be appropriate. Veterinary acceptable salts of the compounds of the instant invention include, but are not limited to: acetate, ascorbate, aspartate, benzoate, besylate, bicarbonate/carbonate, bisulphate/sulphate, borate, camsylate, citrate, edisylate, etoglutarate, esylate, formate, fumarate, gluceptate, gluconate, glucuronate, glycerophosphate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate, and trifluoroacetate salts.

The Chan-Lam reaction (coupling) is a cross-coupling reaction between an aryl boronic acid and an alcohol or an amine to form the corresponding secondary aryl amines or aryl ethers, respectively. The reaction is catalyzed by copper complexes. The Buchwald (Buchwald-Hartwig) reaction is used for the synthesis of C—N bonds via palladium catalyzed coupling reactions of amines with aryl halides.

The compounds of the invention can be prepared as described herein. Schemes 1-7 provide a means for making the compounds and similar analogs.

Scheme 1.
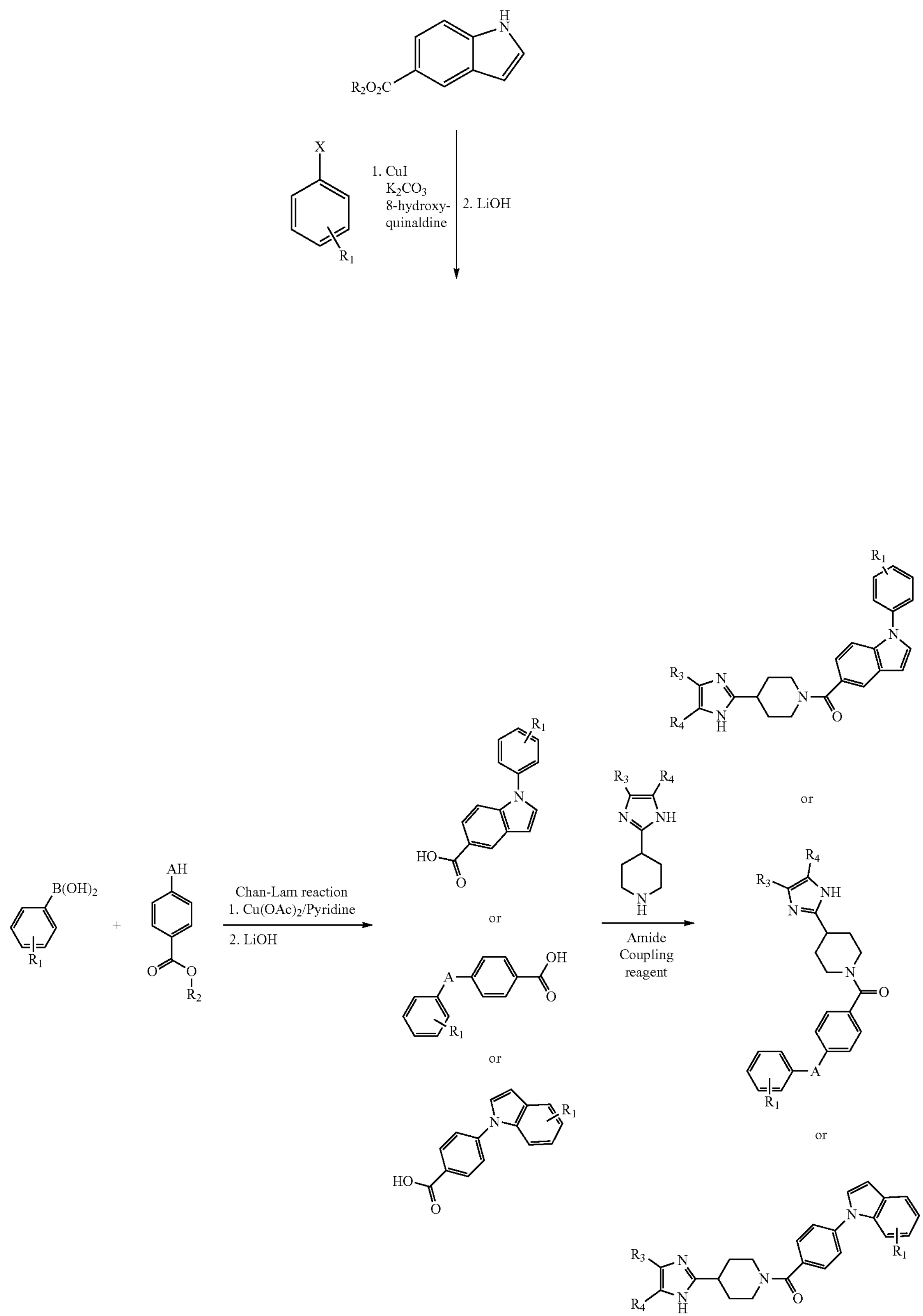

-continued

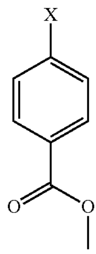

1. Nucleophilic aromatic substitution or Buchwald reaction
2. LiOH

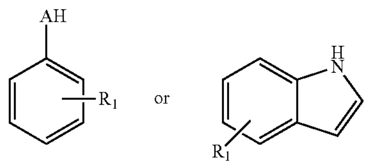

In Scheme 1, compounds with a heteroatom, A, between the 2 aromatic rings can be synthesized using a Chan-Lam reaction between an aryl boronic acid and a phenol or aniline (Tetrahedron Letters, 39(19), 2937-2940; 1998) or by reaction between a substituted phenol or aniline with a halo benzoate under aromatic nucleophilic substitution conditions (X=Cl, F in the presence of a base) or Buchwald type conditions (X=Cl, Br or I) and palladium catalysis, (Castillo, et.al., Chem Rev., 2016, 116 (19) pp 12564-12649). After hydrolysis of the benzoate ester, the acid can be coupled to the substituted piperidine with any of the many known amide coupling agents (e.g., HATU, DIC, EDCl, HBTU, TBTU, HCTU, PyBOP, COMU, $T_3P$, and the like).

Scheme 2.

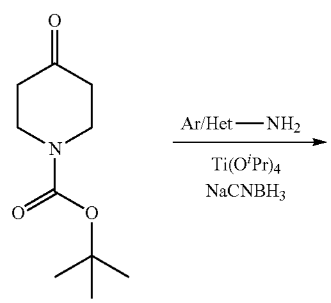

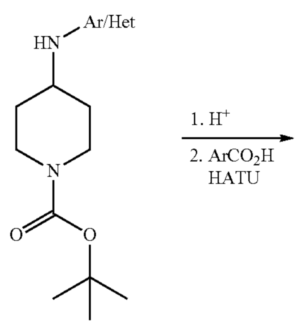

-continued

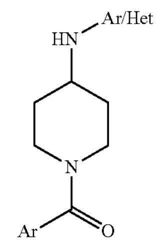

In Scheme 2, the piperidine aminoimidazole was synthesized from the piperidone and amino-imidazole using titanium tetraisopropoxide (to facilitate imine synthesis) followed by reduction using sodium cyanoborohydride (WO2007/014409; p. 19). The free amine was released with HCl and coupled with aryl carboxylic acid with HATU.

Scheme 3.

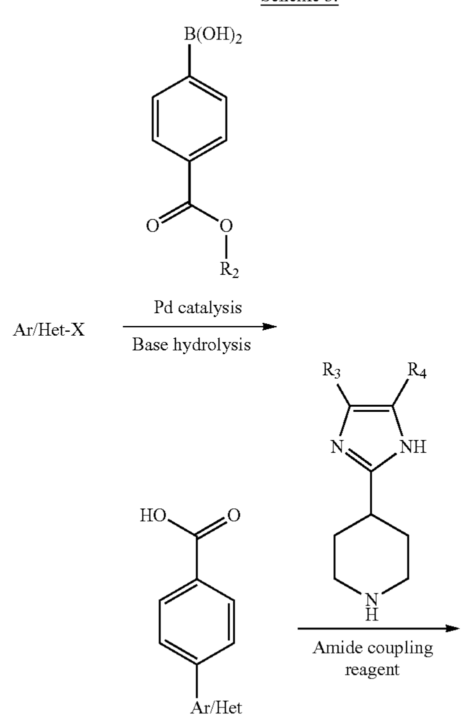

-continued

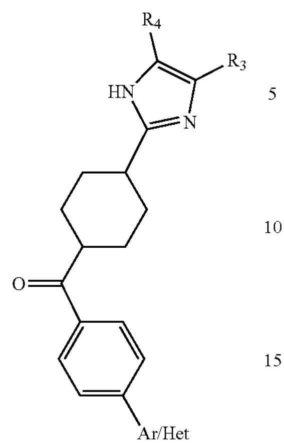

In Scheme 3, the diarylcarboxylic acids can be synthesized using a Suzuki reaction (or other classic aryl coupling reaction such as Stille or Negishi) between a halo (halogen; X) aromatic ring with 1 or more substituents and an aryl boronic acid 4-carboxylate. After hydrolysis of the benzoate ester, the acid is coupled to the substituted piperidine with an amide coupling reagent.

Scheme 4.

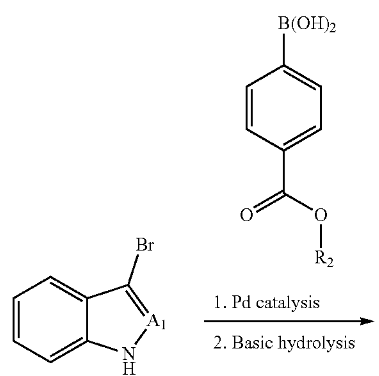

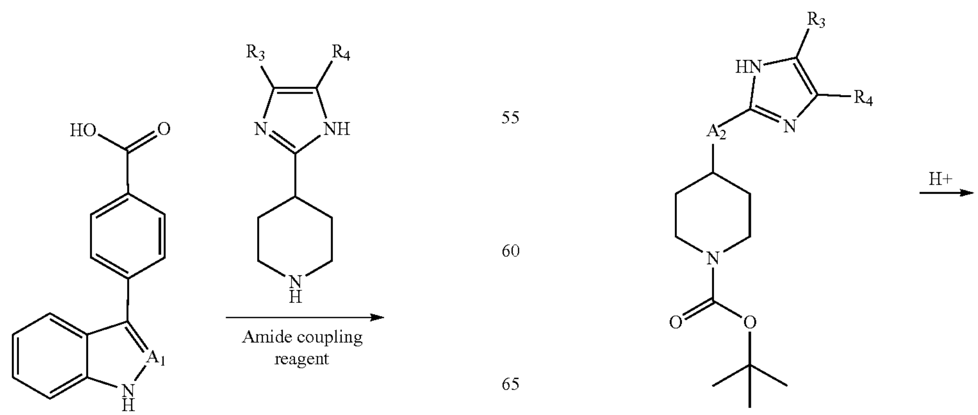

-continued

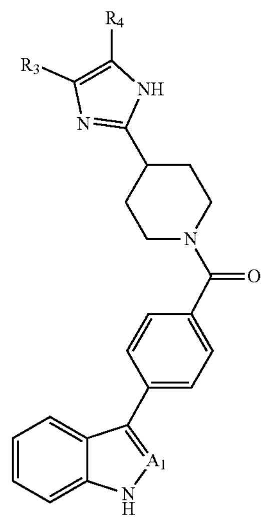

In Scheme 4, the indole/indazole aryl carboxylic acids (where $A_1$=C or N) could be synthesized using a Suzuki reaction (or other classic aryl coupling reaction such as Stille or Negishi) between a halo indole/indazole with zero or more substituents and an aryl boronic acid 4-carboxylate. After hydrolysis of the benzoate ester, the acid is coupled to the substituted piperidine with an amide coupling reagent.

Scheme 5.

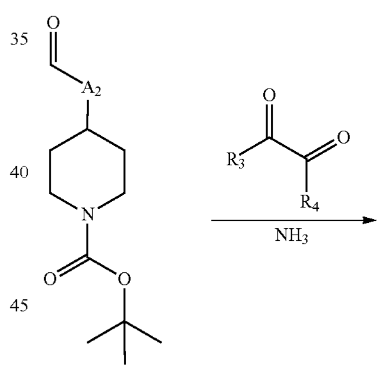

-continued

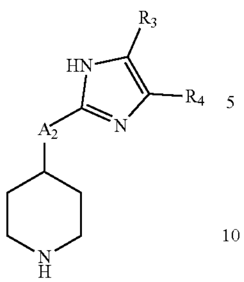

In Scheme 5, the piperidine imidazoles can be synthesized from the readily available Boc protected piperidine aldehydes via reaction with an α-dicarbonyl compound and ammonia. Besides Boc, additional amine protecting groups can be employed to block or protect an amine on the compound thereby protecting its functionality while allowing for the reaction of other functional groups on the compound. Non-exclusive examples of an amine-protecting group include: acyl groups (e.g., formyl, acetyl, chloroacetyl, trichloro-acetyl, o-nitrophenylacetyl, o-nitrophenoxyacetyl, trifluoroacetyl, acetoacetyl, 4-chlorobutyryl, isobutyryl, o-nitrocinnamoyl, picolinoyl, acylisothiocyanate, aminocaproyl, benzoyl, and the like), acyloxy groups (e.g., 1-tert-butyloxycarbonyl (Boc), methoxycarbonyl, 9-fluorenyl-methoxycarbonyl, 2,2,2-trifluoroethoxycarbonyl, 2-trimethylsilylethxoycarbonyl, vinyloxycarbonyl, allyloxycarbonyl, 1,1-dimethyl-propynyloxycarbonyl, benzyloxy-carbonyl, p-nitrobenzyloxycarbony, 2,4-dichlorobenzyloxycarbonyl, and the like), diphenylmethane, and benzylcarbamates. The Boc group (or other amine protecting group) can then be removed with a strong acid (e.g., TFA, HCl, and the like).

Scheme 6

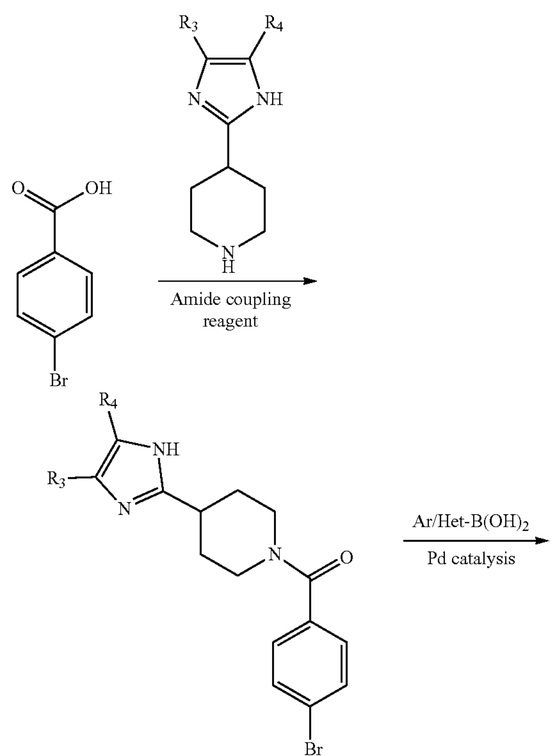

-continued

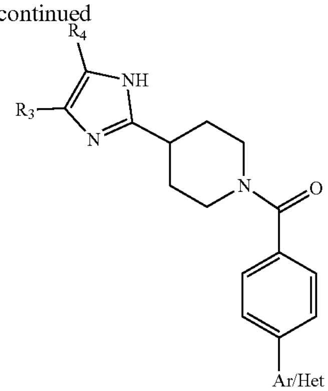

In scheme 6 the bromo-aryl precursor is synthesized by coupling the 4-bromobenzoic acid with the substituted piperidine using an amide coupling reagent. The bromoaryl precursor is then coupled to aryl boronic acids to give the desired diaryl fragment.

Scheme 7

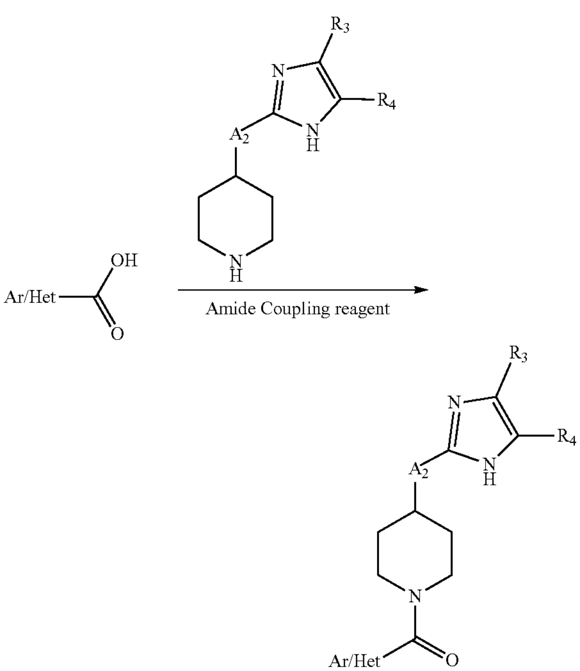

In Scheme 7, the acid can be coupled to the substituted piperidine with any of the many known amide coupling agents (e.g., HATU, DIC, EDCl, HBTU, TBTU, HCTU, PyBOP, COMU, $T_3P$, and the like).

The compounds of the invention are useful as 5-HT2B antagonists for the treatment of MMVP, CHF, and/or asymptomatic heart failure in animals, particularly canines (c5-HT2B). Another aspect of the invention is a veterinary composition comprising a therapeutically effective amount of a compound of the invention, and veterinary acceptable salts thereof. Another aspect of the invention is a veterinary composition comprising a therapeutically effective amount of a compound of the invention, veterinary acceptable salts thereof, and a veterinary acceptable excipient. The compounds of the invention (including the compositions and processes used therein) may also be used in the manufacture of a medicament for the therapeutic applications described herein.

The compounds of the invention can be administered alone or in a formulation appropriate to the specific use envisaged and the species of animal being treated. Generally, it will be administered as a formulation in association with one or more veterinary acceptable excipients. The term "excipient", is used herein to describe any ingredient other than the compound of the invention or any additional veterinary agent. The choice of excipient(s) will to a large extent depend on factors such as the particular mode of administration, the effect of the excipient(s) on solubility and stability, and the nature of the dosage form. In addition to the excipient(s), the amount of the compound of the invention that is administered and the dosage regimen for treating a condition or disorder with the compound depends on a variety of factors, including the age, weight, sex and medical condition of the animal, the severity of the disease, the route and frequency of administration, and thus may vary widely.

In one aspect, the veterinary composition comprises a compound of the invention with a veterinary acceptable excipient. The concentration range will vary depending on the composition (e.g., oral or injectable). For an oral dose, the range of active (i.e., compound of the invention) is about 0.1 to 10 mg/kg, preferably from about 0.5 to 5 mg/kg, and even more preferably from about 0.5 to 3 mg/kg, and most preferably from about 0.5 to about 1.5 mg/kg. For an injectable solution, the range of active is about 0.1 to 50 mg/mL, and preferably from about 0.5 to 25 mg/mL, and more preferably from about 1 to 10 mg/mL, and even more preferably from about 2 to 5 mg/mL. The preferable route of administration is oral. The concentration ranges and preferred concentration ranges are considered to be therapeutically effective doses. Further, dose range and preferred dose range can be hiher or lower than the concentrations described herein.

The formulations can be prepared using conventional dissolution and mixing procedures. Such compositions and methods for their preparation may be found, for example, in 'Remington's Veterinary Sciences', 19th Edition (Mack Publishing Company, 1995; and "Veterinary Dosage Forms: Tablets, Vol. 1", by H. Lieberman and L. Lachman, Marcel Dekker, N.Y., 1980 (ISBN 0-8247-6918-X).

A typical formulation is prepared by mixing a compound of the invention with at least one veterinary acceptable excipient. Suitable excipients are well known to those skilled in the art and include materials such as carbohydrates, waxes, water soluble and/or swellable polymers, hydrophilic or hydrophobic materials, gelatin, oils, solvents, water, and the like. The particular excipient(s) will depend upon the means and purpose for which the compound of the invention is being applied. Solvents are generally selected based on solvents recognized by persons skilled in the art as safe to be administered to an animal. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the invention or veterinary composition thereof) or aid in the manufacturing of the veterinary product (i.e., medicament). The compound of the invention will typically be formulated into veterinary dosage forms to provide an easily controllable dosage form for administration.

The methods by which the compound of the invention may be administered include oral and injectable (e.g., parenteral and subcutaneous).

The compounds of the invention can be administered orally by capsule, bolus, tablet, powders, lozenges, chews, multi and nano-particulates, gels, solid solution, films, sprays, or liquid form. This is a preferred method of administration and as such it is desirable to develop the compound for oral administration. Such formulations may be employed as fillers in soft or hard capsules, soft or hard palatable chews, which typically comprise an excipient, for example, water, ethanol, polyethylene glycol, N-methylpyrrolidone, propylene glycol, methylcellulose, or a suitable oil, and one or more emulsifying agents, flavorants, and/or suspending agents. Liquid forms include suspensions, solutions, syrups, drenches and elixirs. Liquid formulations may also be prepared by the reconstitution of a solid, for example, from a sachet.

Injectable formulations may be prepared in the form of a sterile solution, which may contain other substances, for example enough salts or glucose to make the solution isotonic with blood. Acceptable liquid excipients include vegetable oils such as sesame oil and cotton seed oil, glycerides such as triacetin, esters such as benzyl benzoate, isopropyl myristate and fatty acid derivatives of propylene glycol, as well as organic solvents such as pyrrolidin-2-one, benzyl alcohol and glycerol formal. The formulations are prepared by dissolving or suspending compounds of the invention alone or with an additional veterinary agent in the liquid excipient(s) such that the final formulation contains from about 0.01 to 30% by weight of the active ingredient.

Suitable devices for injectable administration include needle (including micro needle) injectors, needle-free injectors and infusion techniques. Injectable formulations are typically aqueous solutions which may contain excipients such as salts, carbohydrates and buffering agents (preferably to a pH of from 3 to 9), but, for some applications, they may be more suitably formulated as a sterile non-aqueous solution or as a dry powder form to be used in conjunction with a suitable vehicle such as sterile, pyrogen-free water. The preparation of injectable formulations under sterile conditions, for example, by lyophilisation, may readily be accomplished using standard veterinary techniques well known to those skilled in the art. The solubility of a compound of the invention used in the preparation of an injectable solution may be increased by the use of appropriate formulation techniques, such as the incorporation of solubility-enhancing agents.

Administration of the compound of the instant invention is contemplated to be once or twice daily. Preferably, once a day (qd).

The composition of the invention may be administered alone, as described above, or in combination with at least one other additional veterinary agent thereby providing a broader spectrum of veterinary utility. These at least one other additional veterinary agents, including pharmaceutical agents, can be dosed simultaneously with the compound of the invention, or anytime through-out the duration of treatment of the animal.

The following list of additional pharmaceutical (veterinary) cardiovascular agents together with which the compound of the invention can be used to treat cardiac disease (e.g., MMVD, CHF, and/or asymptomatic heart failure) is intended to illustrate the possible combinations, but not to impose any limitation thereof. Non-limiting examples of additional pharmaceutical (veterinary) agents include: diuretics (e.g., furosemide, chlorothiazide, indapamide, triamterene, hydrochlorothiazide, and the like) to reduce edema and effusion; aldosterone antagonists (e.g., spironolactone, eplerenone, and the like) to reduce aldosterone-mediated myocardial fibrosis, possibly slowing the progression of heart disease and block the reabsorption of sodium which encourages water loss; and an ACE inhibitor (e.g. enalapril, accupril, captopril, ramipril, and the like) to inhibit the action of angiotensin-converting enzyme, producing a balanced vasodilation by relaxing blood vessels.

The veterinary composition for application to an animal may be packaged in a variety of ways depending upon the method used for administering the compound of the invention or combination, thereof. Generally, an article for distribution includes a container having deposited therein the veterinary composition in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The compounds of the invention (including the compositions and processes used therein) may also be used in the manufacture of a medicament for the therapeutic applications described herein.

The compound structures in the examples below were confirmed by one or more of the following methods: proton magnetic resonance spectroscopy, and mass spectroscopy. Proton magnetic resonance (1H NMR) spectra were determined using a Bruker spectrometer operating at a field strength of 400 megahertz (MHz). Chemical shifts are reported in parts per million (PPM, 6) downfield from an internal tetramethylsilane standard or residual protonated NMR solvents. Mass spectra (MS) data were obtained using Agilent mass spectrometer (1290 Infinity II) with multimode electrospray and atmospheric pressure chemical ionization (MM-ES+APCI) method. High-performance liquid chromatography (HPLC) performed on Agilent 1260 infinity II with X-Bridge C8 (50×4.6) mm, 3.5 μm column. The mobile phase was a binary gradient of acetonitrile and 10 mM ammonium bicarbonate in water with a flow rate of 1.0 mL/minute.

EXAMPLES

The following examples provide a more detailed description of the process conditions for preparing compounds of the invention. It is to be understood, however, that the invention, as fully described herein and as recited in the claims, is not intended to be limited by the details of the following modes of preparation.

Example 1. (4-((1H-imidazol-2-yl)amino)piperidin-1-yl)(4'-fluoro-[1,1'-biphenyl]-4-yl)methanone (Scheme 2)

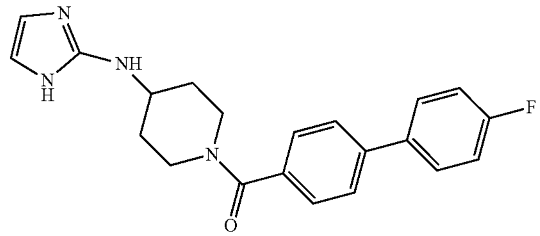 [SMILES: O=C(c1ccc(-c2ccc(F)cc2)cc1)N1CCC(Nc2ncc[nH]2)CC1]

Step 1. Preparation of tert-butyl 4-(1H-imidazol-2-ylamino)piperidine-1-carboxylate A mixture of tert-butyl 4-oxopiperidine-1-carboxylate (5 g, 25.12 mmol), 1H-imidazol-2-amine hydrochloride (4.48 g, 37.68 mmol), trimethylamine (10.31 mL, 75.36 mmol) and titanium(IV) isopropoxide (15.22 mL, 50.24 mmol) was stirred at 25° C. in THF (100 mL) overnight. Sodium cyanoborohydride (2.37 g, 37.68 mmol) and methanol (10 mL) were then added. The reaction mixture was kept at 25° C. for 4 hours. Water (100 mL) and ethyl acetate (100 mL) were added and the organic layer separated and evaporated to give an oil. This was purified by chromatography (5% methanol in DCM) to give the title compound as white solid.

Step 2. Preparation of 4-(1H-Imidazol-2-ylamino)piperidine hydrochloride

Tert-butyl 4-(1H-imidazol-2-ylamino)piperidine-1-carboxylate (1 g, 3.7 mmol) was stirred at 25° C. in 4N HCl in dioxane (10 mL) for 4 hours. The mixture was evaporated to give the title compound as a brown solid.

Step 3. Preparation of Example 1

4'-fluoro-[1,1'-biphenyl]-4-carboxylic acid (500 mg, 2.31 mmol) and N,N-diisopropylethylamine (1.2 mL, 6.94 mmol) were stirred in DMF (20 mL). HATU (1.3 g, 3.47 mmol) was added to it at room temperature and stirred for 10 minutes. 4-(1H-imidazol-2-ylamino)piperidine hydrohloride (701 mg, 3.47 mmol) was then added and the mixture was stirred for 16 hours. On completion of the reaction it was diluted with water (100 mL) and extracted with ethyl acetate (2×50 mL). The organic portion was dried, concentrated and the residue purified by flash column chromatography (5% methanol in DCM) to give title compound as a white solid. 1H NMR ($d_6$-DMSO, 400 MHz): δ ppm 11.95 (bs, 1H), 7.94 (d, 1H), 7.78-7.73 (m, 4H), 7.49 (d, 2H), 7.33 (t, 2H), 6.99 (s, 2H), 4.50 (bs, 1H), 3.8-3.6 (m, 2H), 3.16-2.97 (m, 2H), 2.1-1.8 (m, 2H), 1.6-1.4 (m, 2H). LC-MS (m/z): [M+H]=365.1.

Example 2. (4-(1H-imidazol-2-yl)piperidin-1-yl)(3'-(methylsulfonyl)-[1,1'-biphenyl]-4-yl)methanone (Scheme 3)

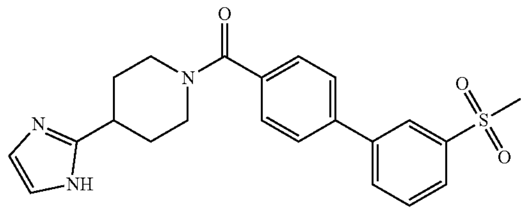 [SMILES: CS(=O)(=O)c1cccc(-c2ccc(C(=O)N3CCC(c4ncc[nH]4)CC3)cc2)c1]

Step 1. Preparation of methyl 3'-(methylthio)-[1,1'-biphenyl]-4-carboxylate

To a stirred solution of (3-bromophenyl)(methyl)sulfane (1.5 g, 7.38 mmol) and (4-(methoxycarbonyl)phenyl)boronic acid (1.72 g, 9.6 mmol) in DMF (10 mL) added $K_3PO_4$ (4.69 g, 22.1 mmol) at 25° C. The reaction mixture was saturated with argon for 10 minutes. $PdCl_2$(dppf)DCM (301 mg, 0.36 mmol) was added to it and stirred at 80° C. for 16 hours. The reaction was monitored by TLC and LCMS. On completion of the reaction it was diluted with water (100 mL) and extracted with ethyl acetate (2×100 mL). The organic portion was dried, concentrated and the residue purified by flash column chromatography (30% ethyl acetate in hexane) to give the title compound as white solid.

Step 2. Preparation of methyl 3'-(methylsulfonyl)-[1,1'-biphenyl]-4-carboxylate

To a stirred solution of methyl 3'-(methylthio)-[1,1'-biphenyl]-4-carboxylate (1 g, 3.8 mmol) in methanol/$H_2O$ (20+8 mL) added potassium peroxymonosulfate compound ($KHSO_5$.0.5$KHSO_4$.0.5$K_2SO_4$, Oxone®) (3.5 g, 11.6 mmol) at 25° C. The reaction mixture stirred at 25° C. for 16 hours. The reaction was monitored by TLC and LCMS. On completion of the reaction it was evaporated to get crude reaction mixture. It was diluted with ethyl acetate 100 mL and washed with brine. The organic portion was dried, concentrated and the residue purified by flash column chromatography (25% ethyl acetate in hexane) to give the title compound as white solid.

Step 3. Preparation of 3'-(methylsulfonyl)-[1,1'-biphenyl]-4-carboxylic acid

To a stirred solution of methyl 3'-(methylsulfonyl)-[1,1'-biphenyl]-4-carboxylate (1 g, 3.4 mmol) in THF/methanol/$H_2O$ (12+4+2 mL) added lithium hydroxide monohydrate (434 mg, 10.3 mmol) at 25° C. The reaction mixture stirred at 25° C. for 16 hours. The reaction was monitored by TLC and LCMS. On completion of the reaction it was evaporated to get crude reaction mixture. It was acidified with 1N HCl (10 mL) at 0° C. The resulted solids were filtered and washed with water to give the title compound as white solid. The crude title compound was used in next step without further purification.

Step 4. Preparation of Example 2

3'-(methylsulfonyl)-[1,1'-biphenyl]-4-carboxylic acid (500 mg, 1.81 mmol) and N,N-diisopropylethylamine (0.98 mL, 5.43 mmol) were stirred in DMF (10 mL). HATU (1.03 g, 2.71 mmol) was added to it at room temperature and stirred for 10 minutes. 4-(1H-imidazol-2-yl)piperidine hydrochloride salt (460 mg, 2.41 mmol (Scheme 5)) was then added and the mixture stirred for 16 hours at room temperature. The reaction was monitored by TLC and LCMS. On completion of the reaction it was diluted with ethyl acetate (100 mL) and washed with water (2×50 mL). The organic portion was dried, concentrated and the residue purified by flash column chromatography (3% methanol in DCM) to give the title compound as white solid. $^1$H NMR ($d_6$-DMSO, 400 MHz): δ ppm 13.19 (bs, 1H), 8.2 (s, 1H), 8.09 (d, 1H), 7.95 (d, 1H), 7.87 (d, 2H), 7.78 (t, 1H), 7.55 (d, 2H), 7.20 (s, 2H), 4.54 (bs, 1H), 3.72-3.71 (m, 1H), 3.31 (s, 3H), 3.17-3.11 (m, 2H), 2.98 (bs, 1H), 2.02-1.91 (m, 2H), 1.73 (bs, 2H). LC-MS (m/z): [M+H]=410.1.

Example 3. (4-(1H-imidazol-2-yl)piperidin-1-yl)(4'-(trifluoromethyl)-[1,1'-biphenyl]-4-yl)methanone (Scheme 7)

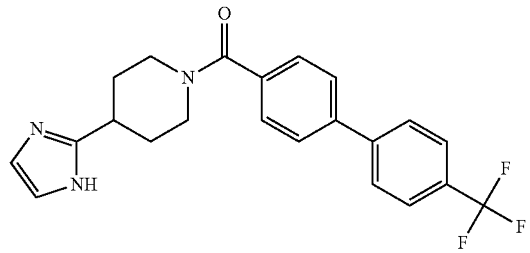 [SMILES: O=C(c1ccc(-c2ccc(C(F)(F)F)cc2)cc1)N1CCC(c2ncc[nH]2)CC1]

4'-(trifluoromethyl)-[1,1'-biphenyl]-4-carboxylic acid (18 g, 67.61 mmol) and N,N-diisopropylethylamine (37 mL, 202 mmol) were stirred in DMF (200 mL). HATU (38.5 g, 101 mmol) was added to it at room temperature and stirred for 10 minutes. 4-(1H-imidazol-2-yl)piperidine hydrochloride salt (14 g, 74.37 mmol) was then added and the mixture stirred for 16 hours at room temperature. The reaction was monitored by TLC and LCMS. On completion of the reaction it was diluted with ethyl acetate (1000 mL) and washed with water (2×500 mL). The organic portion was dried, concentrated and the residue purified by flash column chromatography (3% methanol in DCM) to give the title compound as white solid. $^1$H NMR ($d_6$-DMSO, 400 MHz): δ ppm 13.97 (bs, 1H), 7.95 (d, 2H), 7.87-7.84 (m, 4H), 7.61 (s, 2H), 7.55 (d, 2H), 4.60 (bs, 1H), 3.73-3.71 (m, 1H), 3.36-3.21 (m, 2H), 2.96 (bs, 1H), 2.08-1.98 (m, 2H), 1.79-1.74 (m, 2H). LC-MS (m/z): [M+H]=400.1.

Example 4. (4-(5-methyl-1H-imidazol-2-yl)piperidin-1-yl)(4'-(trifluoromethyl)-[1,1'-biphenyl]-4-yl)methanone (Scheme 7)

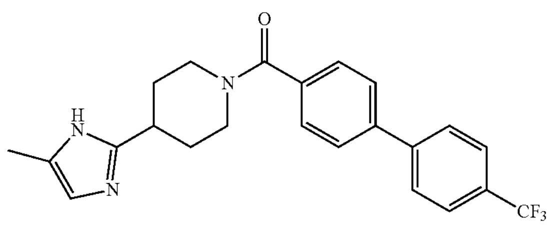 [SMILES: Cc1cnc(C2CCN(C(=O)c3ccc(-c4ccc(C(F)(F)F)cc4)cc3)CC2)[nH]1]

4'-(trifluoromethyl)-[1,1'-biphenyl]-4-carboxylic acid (350 mg, 1.31 mmol) and N,N-diisopropylethylamine (0.72 mL, 4.05 mmol) were stirred in DMF (10 mL). HATU (746 mg, 1.96 mmol) was added to it at room temperature and stirred for 10 minutes. 4-(5-methyl-1H-imidazol-2-yl)piperidinehydrochloride (319 mg, 1.57 mmol) was then added and the mixture was stirred for 16 hours. On completion of the reaction; it was diluted with water (100 mL) and extracted with ethyl acetate (2×50 mL). The organic portion was dried, concentrated and the residue purified by flash column chromatography (5% methanol in DCM) to give title compound as a brown solid. 1H NMR ($d_6$-DMSO, 400 MHz): δ ppm 7.94 (d, 2H), 7.83 (t, 4H), 7.53 (d, 2H), 6.72 (s, 1H), 4.48 (bs, 1H), 3.66 (bs, 1H), 3.31-2.90 (m, 3H), 2.11 (s, 3H), 1.99-1.87 (m, 2H), 1.70-1.60 (m, 2H). LC-MS (m/z): [M+H]=414.2.

Example 5. (4-(1H-indol-3-yl)phenyl)(4-(5-methyl-1H-imidazol-2-yl)piperidin-1-yl)methanone (Scheme 4)

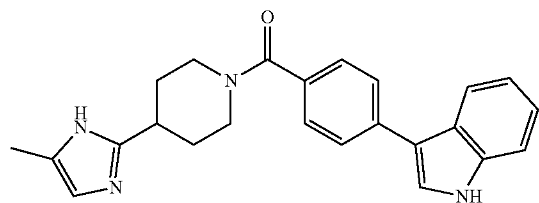 [SMILES: Cc1cnc(C2CCN(C(=O)c3ccc(-c4c[nH]c5ccccc45)cc3)CC2)[nH]1]

Step 1. Preparation of tert-butyl 3-(4-(methoxycarbonyl)phenyl)-1H-indole-1-carboxylate To a stirred solution of tert-butyl 3-bromo-1H-indole-1-carboxylate (1 g, 3.37 mmol) and (4-(methoxycarbonyl) phenyl)boronic acid (725 mg, 4.05 mmol) in DME/$H_2O$ (18+2 mL) added $Na_2CO_3$ (1.07 g, 10.13 mmol) at 25° C. The reaction mixture was saturated with argon for 10 minutes. $Pd(Ph_3P)_4$ (390 mg, 0.33 mmol) was added to it and stirred at 85° C. for 16 hours. The reaction was monitored by TLC & LCMS. On completion of the reaction; it was diluted with water (50 mL) and extracted with ethyl acetate (2×100 mL).

The organic portion was dried, concentrated and the residue purified by flash column chromatography (30% ethyl acetate in hexane) to give the title compound as white solid.

Step 2. Preparation of 4-(1H-indol-3-yl)benzoic acid

To a stirred solution of tert-butyl 3-(4-(methoxycarbonyl) phenyl)-1H-indole-1-carboxylate (500 mg, 1.42 mmol) in THF/methanol/$H_2O$ (12+4+2 mL) added lithium hydroxide monohydrate (180 mg, 4.27 mmol) at 25° C. The reaction mixture stirred at 25° C. for 16 hours. The reaction was monitored by TLC. On completion of the reaction; it was evaporated to get crude reaction mixture. It was acidified with 1N HCl (10 mL) at 0° C. The resulted solids were filtered and washed with water to give the title compound as white solid. The crude title compound was used in next step without further purification.

Step 3. Preparation of Example 5

4-(1H-indol-3-yl)benzoic acid (280 mg, 1.18 mmol) and N,N-diisopropylethylamine (0.64 mL, 3.54 mmol) were stirred in DMF (10 mL). HATU (672 mg, 1.77 mmol) was added to it at room temperature and stirred for 10 minutes. 4-(5-methyl-1H-imidazol-2-yl)piperidine hydrochloride (308 mg, 1.53 mmol) was then added and the mixture was stirred for 16 hours. On completion of the reaction; it was diluted with water (1000 mL) and extracted with ethyl acetate (2×500 mL). The organic portion was dried, concentrated and the residue purified by flash column chromatography (5% methanol in DCM) to give title compound as a white solid. 1H NMR ($d_6$-DMSO, 400 MHz): δ ppm 11.45 (bs, 2H), 7.90 (d, 1H), 7.79-7.75 (m, 3H), 7.46-7.44 (m, 3H), 7.18-7.09 (m, 2H), 6.54 (bs, 1H), 4.45 (bs, 1H), 3.83 (bs, 1H), 3.32-2.86 (m, 3H), 2.07 (s, 3H), 1.90 (bs, 2H), 1.75-1.60 (m, 2H). LC-MS (m/z): [M+H]=385.1.

Example 6. (4-(1H-indazol-3-yl)phenyl)(4-(5-methyl-1H-imidazol-2-yl)piperidin-1-yl)methanone (Scheme 4)

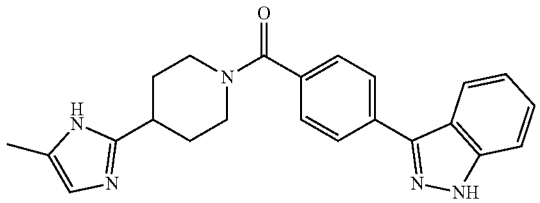 [SMILES: Cc1cnc(C2CCN(C(=O)c3ccc(-c4n[nH]c5ccccc45)cc3)CC2)[nH]1]

Step 1. Preparation of methyl 4-(1H-indazol-3-yl)benzoate

To a stirred solution of 3-bromo-1H-indazole (1.5 g, 7.6 mmol) and (4-(methoxycarbonyl)phenyl)boronic acid (1.5 g, 8.3 mmol) in toluene/ethanol/$H_2O$ (15+5+2 mL) added $Na_2CO_3$ (2.4 g, 22.8 mmol) at 25° C. The reaction mixture was saturated with argon for 10 minutes. $Pd(Ph_3P)_4$ (870 mg, 0.7 mmol) was added to it and stirred at 100° C. for 16 hours. The reaction was monitored by TLC and LCMS. On completion of the reaction; it was diluted with water (50 mL) and extracted with ethyl acetate (2×100 mL). The organic portion was dried, concentrated and the residue purified by flash column chromatography (30% ethyl acetate in hexane) to give the title compound as pale yellow solid.

Step 2. Preparation of 4-(1H-indazol-3-yl)benzoic acid

To a stirred solution of methyl 4-(1H-indazol-3-yl)benzoate (990 mg, 3.92 mmol) in THF/methanol/$H_2O$ (15+5+2 mL) added lithium hydroxide monohydrate (824 mg, 19.62 mmol) at 25° C. The reaction mixture stirred at 25° C. for 16 hours. The reaction was monitored by TLC. On completion of the reaction, it was evaporated to get crude reaction mixture. It was acidified with 1N HCl (10 mL) at 0° C. The resulted solids were filtered and washed with water to give the title compound as white solid. The crude title compound was used in next step without further purification.

Step 3. Preparation of Example 6

4-(1H-indazol-3-yl)benzoic acid (900 mg, 3.78 mmol) and N,N-diisopropylethylamine (2.07 mL, 11.3 mmol) were stirred in DMF (20 mL). HATU (2.1 g, 5.67 mmol) was added to it at room temperature and stirred for 10 minutes.

4-(5-methyl-1H-imidazol-2-yl)piperidine hydrochloride (912 mg, 4.53 mmol) was then added and the mixture was stirred for 16 hours. On completion of the reaction, it was diluted with water (100 mL) and extracted with ethyl acetate (2×50 mL). The organic portion was dried, concentrated and the residue purified by flash column chromatography (5% methanol in DCM) to give title compound as an off-white solid. 1H NMR ($d_6$-DMSO, 400 MHz): δ ppm 13.34 (s, 1H), 11.54 (bs, 1H), 8.1-8.06 (m, 3H), 7.60 (d, 1H), 7.54 (d, 2H), 7.43 (t, 1H), 7.23 (t, 1H), 6.57 (s, 1H), 4.49 (bs, 1H), 3.78 (bs, 1H), 3.25-3.1 (m, 1H), 2.85-3.0 (m, 2H), 2.08 (s, 3H), 1.97-1.80 (m, 2H), 1.70-1.60 (m, 2H). LC-MS (m/z): [M+H]= 386.2.

Example 7. (4-((1H-imidazol-2-yl)amino)piperidin-1-yl)(4'-(trifluoromethyl)-[1,1'-biphenyl]-4-yl)methanone (Scheme 2)

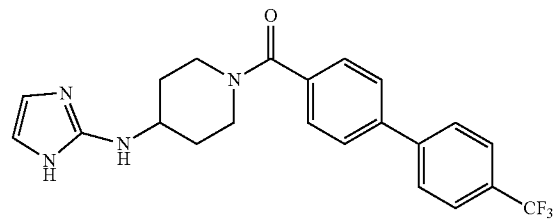 [SMILES: O=C(c1ccc(-c2ccc(C(F)(F)F)cc2)cc1)N1CCC(Nc2ncc[nH]2)CC1]

4'-(trifluoromethyl)-[1,1'-biphenyl]-4-carboxylic acid (450 mg, 1.69 mmol), and N,N-diisopropylethylamine (0.92 mL, 5.07 mmol) were stirred in DMF (10 mL). HATU (960 mg, 2.53 mmol) was added to it at room temperature and stirred for 10 minutes. 4-(1H-imidazol-2-ylamino)piperidine hydrochloride (384 mg, 2.19 mmol) was then added and the mixture stirred for 16 hours. The reaction was monitored by TLC and LCMS. On completion of the reaction it was diluted with ethyl acetate (100 mL) and washed with water (2×50 mL). The organic portion was dried, concentrated and the residue purified by flash column chromatography (5% methanol in DCM)) to give the title compound as white solid. $^1$H NMR ($d_6$-DMSO, 400 MHz): δ ppm 11.93 (bs, 1H), 7.95 (d, 2H), 7.89-7.83 (m, 5H), 7.54 (d, 2H), 6.98 (s, 2H), 4.41 (bs, 1H), 3.66-3.61 (m, 2H), 3.22-2.95 (m, 2H), 2.00-1.91 (m, 2H), 1.47 (bs, 2H), LC-MS (m/z): [M+H]= 415.1

Example 8. (4-(1H-imidazol-2-yl)piperidin-1-yl)(4-phenoxyphenyl)methanone (Scheme 7)

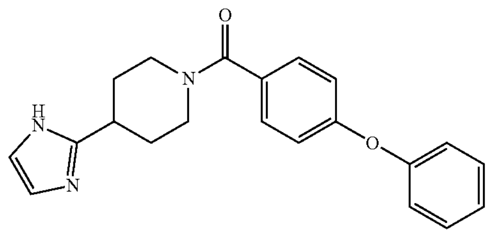 [SMILES: O=C(c1ccc(Oc2ccccc2)cc1)N1CCC(c2ncc[nH]2)CC1]

4-phenoxybenzoic acid (95 mg, 0.4435 mmol, 100 mass %), HATU (253 mg., 0.6653 mmol) and N,N-diisopropylethylamine (0.232 mL, 1.331 mmol, 100 mass %) were stirred in N,N-dimethylformamide (5 mL, 64.6 mmol, 100 mass %) for 10 minutes. 4-(1H-imidazol-2-yl)piperidine (67 mg, 0.4435 mmol) in N,N-dimethylformamide (5 mL, 64.6 mmol, 100 mass %) was added to it at room temperature and stirred for 24 hours. The solution was partitioned between DCM (20 mL) and a saturated water solution of $NaHCO_3$ (20 mL), separated and evaporated. The residue was purified by HPLC purification to give [4-(1H-imidazol-2-yl)-1-piperidyl]-(4-phenoxyphenyl)methanone; 2,2,2-trifluoroacetic acid as a solid gum. This was then partitioned between DCM (10 mL) and a saturated water solution of $NaHCO_3$ (10 mL), and the organic layer separated and evaporated to give a gum, which was dissolved in tBME and evaporated to give the titled compound as a white crystalline solid. 1H NMR (d6-DMSO, 400 MHz): δ ppm 12.5 (bs, 1H), 7.4-7.5 (m, 4H), 7.78 (t, 1H), 7.2-7.3 (m, 1H), 6.9-7.2 (m, 6H), 4.5 (bs, 1H), 2.8-4.0 (m, 6H), 2.0-1.9 (m, 2H), 1.8-1.9 (m, 2H). LC-MS (m/z): [M+H]=348.3.

Example 9. (4-(1H-imidazol-2-yl)piperidin-1-yl)(4-(phenylamino)phenyl)methanone (Scheme 1)

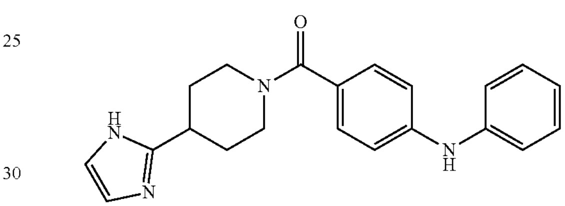

Step 1. Preparation of methyl 4-anilinobenzoate

A mixture of ethyl 4-aminobenzoate (1 g, 6.0536 mmol), phenylboronic acid (2 equiv., 1.48 g, 12.107 mmol), copper (II) acetate (1.5 equiv., 1.65 g, 9.0805 mmol), molecular sieves (4 A, activated, 100 mg), pyridine (4 equiv., 1.96 mL, 24.215 mmol, 100 mass %) in dichloromethane (30 mL) was stirred at room temperature in dry air for 4 days. The mixture was diluted with DCM, washed with 5% ammonia solution, filtered through silica and $MgSO_4$ and concentrated under reduced pressure to give an orange oil. The residue was purified by chromatography (DCM) to give the title compound as a white waxy solid.

Step 2. Preparation of 4-anilinobenzoic acid

Ethyl 4-anilinobenzoate (C, 617 mg, 2.714 mmol, 100 mass %) was dissolved in methanol (10 mL) and had 2M sodium hydroxide in water (4 equiv., 5.1 mL, 10.86 mmol) added to it and heated up to 70° C. over 30 minutes before cooling to room temperature and stirring for 3 days. 2M HCl (aq) (10 mL) was added and the mixture extracted with DCM and evaporated to give 4-anilinobenzoic acid as a white solid.

Step 3. Preparation of Example 9

4-anilinobenzoic acid (150 mg, 0.7036 mmol), HATU (1.5 equiv., 4.1 mg, 1.055 mmol) and N,N-diisopropylethylamine (5 equiv., 0.61 mL, 3.518 mmol) were stirred in N,N-dimethylformamide (2 mL) for 10 min. 4-(1H-imidazol-2-yl)piperidine; 2,2,2-trifluoroacetic acid (E, 1.2 equiv., 517 mg, 0.8443 mmol, 62 mass %) was added to it at room temperature and stirred for 7 days. The solution was purified by SFC purification to give (4-anilinophenyl)-[4-(1H-imidazol-2-yl)-1-piperidyl]methanone as a white solid 1H NMR (d6-DMSO, 400 MHz): δ ppm 11.8 (bs, 1H), 8.45 (s, 1H), 7.28 (t, 4H), 7.14 (d, 2H), 7.06 (d, 2H), 6.94-6.83 (m, 3H), 4.1 (bs, 1H), 3.15-2.9 (m, 3H), 1.97-1.85 (m, 3H), 1.73-1.57 (m, 2H). LC-MS (m/z): [M+H]=347.2.

Example 10. (4-(1H-imidazol-2-yl)piperidin-1-yl)(3'-chloro-[1,1'-biphenyl]-4-yl)methanone; trifluoroacetic acid salt, (Scheme 7)

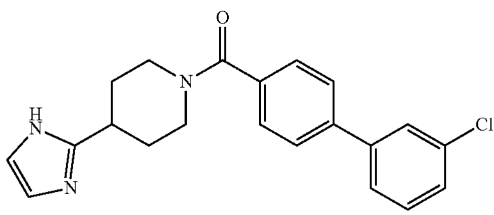 [SMILES: O=C(c1ccc(-c2cccc(Cl)c2)cc1)N1CCC(c2ncc[nH]2)CC1]

This compound was synthesized in a similar manner to the procedure in Example 3 except that 3'-chloro-[1,1'-biphenyl]-4-carboxylic acid was used instead of 4'-(trifluoromethyl)-[1,1'-biphenyl]-4-carboxylic acid and the final material was purified by preparative HPLC with TFA as a modifier. 1H NMR (d6-DMSO, 400 MHz): δ ppm 14.1 (s, 2H), 7.83-7.75 (m, 3H), 7.7 (d, 1H), 7.64 (s, 2H), 7.56-7.45 (m, 4H), 4.6 (bs, 1H), 3.8-2.8 (m, 4H), 2.2-1.9 (m, 2H), 1.90-1.7 (m, 2H). LC-MS (m/z): [M+H]=366.1.

Example 11. (4-(1H-imidazol-2-yl)piperidin-1-yl)(6-phenylpyridin-3-yl)methanone, trifluoroacetic acid salt (Scheme 7)

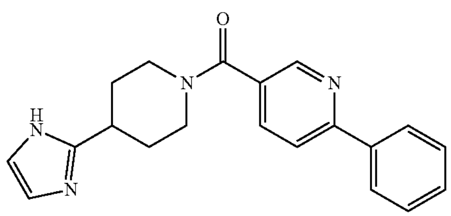 [SMILES: O=C(c1ccc(-c2ccccc2)nc1)N1CCC(c2ncc[nH]2)CC1]

This compound was synthesized in a similar manner to the procedure in Example 3, except that 6-phenylnicotinic acid was used instead of 4'-(trifluoromethyl)-[1,1'-biphenyl]-4-carboxylic acid and the final material was purified by preparative HPLC with TFA as a modifier. 1H NMR (d4-MeOD, 400 MHz): δ ppm 8.73 (s, 1H), 8.1-7.95 (m, 4H), 7.6-7.45 (m, 5H), 3.95 (bs, 1H), 3.5-3.4 (m, 2H), 3.2-3.0 (m, 1H), 2.3-2.0 (m, 2H), 2.0-1.8 (m, 2H). LC-MS (m/z): [M+H]=333.2.

Example 12. (4-((1H-imidazol-2-yl)methyl)piperidin-1-yl)(4'-(trifluoromethyl)-[1,1'-biphenyl]-4-yl)methanone, trifluoroacetic acid salt (Scheme 7)

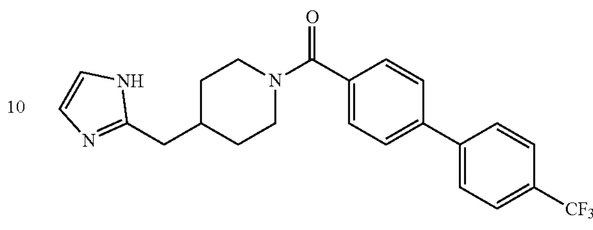

This compound was synthesized in a similar manner to the procedure in Example 3, except that 4-((1H-imidazol-2-yl)methyl)piperidine hydrochloride salt was used instead of 4-((1H-imidazol-2-yl)piperidine hydrochloride salt. 1H NMR (d6-DMSO, 400 MHz): δ ppm 13.95 (bs, 1H), 7.95 (d, 2H), 7.9-7.8 (m, 4H), 7.58 (s, 2H), 7.51 (d, 2H), 4.5 (bs, 1H), 3.63 (bs, 1H), 3.1 (bs, 1H), 2.88 (d, 2H), 2.8 (bs, 1H), 2.15-2.0 (m, 1H), 1.70-1.45 (m, 2H), 1.3-1.15 (m, 2H). LC-MS (m/z): [M+H]=414.4.

Example 13. (4-(1H-imidazol-2-yl)piperidin-1-yl)(4-(benzo[d][1,3]dioxol-5-yl)phenyl)methanone, trifluoroacetic acid salt (Scheme 3)

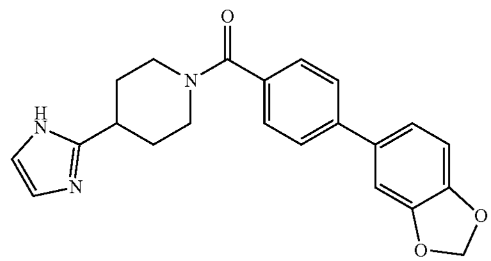 [SMILES: O=C(c1ccc(-c2ccc3c(c2)OCO3)cc1)N1CCC(c2ncc[nH]2)CC1]

This compound was synthesized in a similar manner to the procedure in Example 2 (Step 1) except that 5-bromobenzo[d][1,3]dioxole was used instead of (3-bromophenyl)(methyl)sulfane and there was no oxidation step and the final material was purified by preparative HPLC with TFA as a modifier. 1H NMR (d4-MeOD, 400 MHz): 5 ppm 7.7 (d, 2H), 7.55-7.45 (m, 4H), 7.2-7.15 (m, 2H), 6.94 (d, 1H), 6.02 (s, 2H), 4.0 (bs, 1H), 3.5-3.4 (m, 1H), 3.2-3.0 (m, 1H), 2.3-2.0 (m, 2H), 2.0-1.80 (bs, 2H). LC-MS (m/z): [M+H]=376.1.

Example 14. (4-(1H-imidazol-2-yl)piperidin-1-yl)(9H-carbazol-2-yl)methanone (Scheme 7)

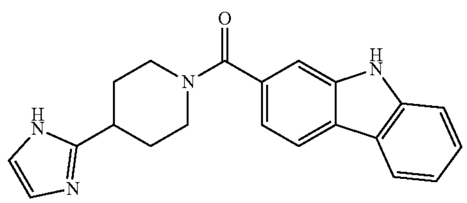 [SMILES: O=C(c1ccc2c(c1)[nH]c1ccccc12)N1CCC(c2ncc[nH]2)CC1]

This compound was synthesized in a similar manner to the procedure in Example 3, except that 9H-carbazole-2-carboxylic acid was used instead of 4'-(trifluoromethyl)-[1,1'-biphenyl]-4-carboxylic acid. 1H NMR (d6-DMSO, 400 MHz): δ ppm 11.98 (bs, 1H), 11.39 (s, 1H), 8.2-8.1 (m, 2H), 7.55-7.45 (m, 2H), 7.42 (t, 1H), 7.25-7.15 (m, 2H), 6.93 (s, 2H), 4.5 (bs, 1H), 3.8 (bs, 1H), 3.2-2.95 (m, 3H), 2.0-1.8 (m, 2H), 1.8-1.60 (m, 2H). LC-MS (m/z): [M+H]=345.2.

Example 15. (4-(1H-imidazol-2-yl)piperidin-1-yl)(dibenzo[b,d]furan-3-yl)methanone, trifluoroacetic acid salt (Scheme 7)

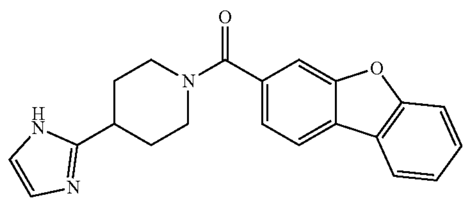 [SMILES: O=C(c1ccc2c(c1)oc1ccccc12)N1CCC(c2ncc[nH]2)CC1]

This compound was synthesized in a similar manner to the procedure in Example 3, except that dibenzo[b,d]furan-3-carboxylic acid was used instead of 4'-(trifluoromethyl)-[1,1'-biphenyl]-4-carboxylic acid, and the final material was purified by preparative HPLC with TFA as a modifier. 1H NMR (d6-DMSO, 400 MHz): δ ppm 14.06 (s, 2H), 8.3-8.2 (m, 2H), 7.8-7.7 (m, 2H), 7.65 (s, 2H), 7.61 (t, 1H), 7.5-7.4 (m, 2H), 4.68 (bs, 1H), 3.7 (bs, 2H), 2.97 (bs, 2H), 2.2-1.9 (m, 2H), 1.9-1.75 (m, 2H). LC-MS (m/z): [M+H]=346.1.

Example 16. (4-(1H-imidazol-2-yl)piperidin-1-yl)(4'-(difluoromethyl)-[1,1'-biphenyl]-4-yl)methanone (Scheme 3)

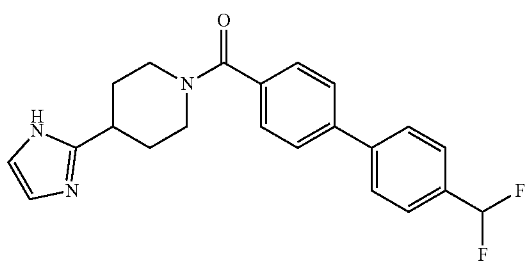 [SMILES: O=C(c1ccc(-c2ccc(C(F)F)cc2)cc1)N1CCC(c2ncc[nH]2)CC1]

This compound was synthesized in a similar manner to the procedure in Example 2 (Step 1) except that 1-bromo-4-(difluoromethyl)benzene was used instead of (3-bromophenyl)(methyl)sulfane and there was no oxidation step. 1H NMR (d6-DMSO, 400 MHz): δ ppm 11.72 (s, 1H), 7.87 (d, 2H), 7.8 (d, 2H), 7.69 (d, 2H), 7.53 (d, 2H), 7.1 (t, 1H), 7.0 (s, 1H), 6.77 (s, 1H), 4.48 (bs, 1H), 3.7 (bs, 1H), 3.22 (bs, 1H), 3.1-2.9 (m, 2H), 2.05-1.8 (m, 2H), 1.8-1.60 (m, 2H). LC-MS (m/z): [M+H]=382.2.

Example 17. (4-(1H-imidazol-2-yl)piperidin-1-yl)(4-(1H-indol-4-yl)phenyl)methanone (Scheme 6)

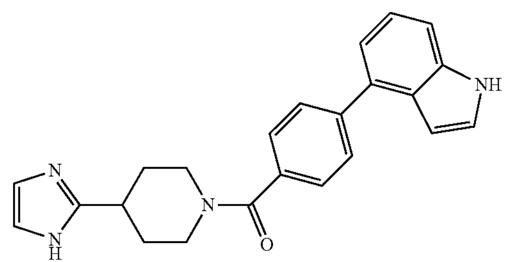 [SMILES: O=C(c1ccc(-c2cccc3[nH]ccc23)cc1)N1CCC(c2ncc[nH]2)CC1]

Step-1. Preparation of (4-(1H-imidazol-2-yl)piperidin-1-yl)(4-bromophenyl)methanone To a stirred solution of 4-bromobenzoic acid (200 mg, 1 mmol) in DMF (10 mL) was added HATU (570 mg, 1.5 mmol). The reaction mixture was stirred at room temperature for 15 minutes under nitrogen atmosphere and further cooled to 0° C. DIPEA (0.55 mL, 3 mmol) and compound 4-(1H-imidazol-2-yl)piperidine (151 mg, 1 mmol) was added to the above reaction mixture and stirred for 16 hours. The reaction mixture was diluted with excess of DCM and given water and brine solution wash, dried over anhydrous sodium sulphate and concentrated to obtain crude product. The crude was purified by column chromatography. ($SiO_2$ 230-400) Compound was eluted by using 5% MeOH in DCM as eluent to give the title compound as a white solid.

Step-2. Preparation of Example 17

A 10 mL tensil seal tube was charged with 3 (90 mg, 0.270 mmol), 4 (52 mg, 0.216 mmol), sodium carbonate (25 mg, 0.810 mmol) and Pd(dppf)$Cl_2$DCM (22 mg, 0.027 mmol), dioxane (6 mL) and water (3 mL) under nitrogen. Reaction mixture was purged with nitrogen gas for 5 minutes and was sealed. Reaction mixture was heated at 65° C. for 30 minutes. Reaction mixture was cooled to room temperature and partitioned between DCM (30 mL) and water (20 mL). Aqueous layer was extracted with DCM (10 mL×2). Combined organic layer was washed with brine (10 mL) dried over $Na_2SO_4$ and concentrated under reduced pressure to get 130 mg of brown solid as a crude. The crude product was purified by preparative-HPLC purification. Product containing fraction were freeze dried to give the title compound as off-white solid. 1H NMR (d4-MeOD, 400 MHz): δ ppm 7.8 (d, 2H), 7.55 (d, 2H), 7.42 (d, 1H), 7.31 (d, 1H), 7.25-7.15 (m, 1H), 7.15-7.05 (m, 3H), 6.6 (d, 1H), 4.8 (bs, 1H), 4.02 (bs, 1H), 3.25-3.0 (m, 2H), 2.25-1.75 (m, 4H). LC-MS (m/z): [M+H]=371.2.

Example 18. (4-(1H-imidazol-2-yl)piperidin-1-yl)(4-(1H-indol-1-yl)phenyl)methanone (Scheme 1)

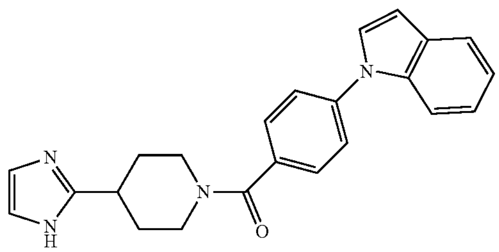 [SMILES: O=C(c1ccc(-n2ccc3ccccc32)cc1)N1CCC(c2ncc[nH]2)CC1]

Step 1. Preparation of 4-(1H-indol-1-yl)benzoic acid

To a stirred solution of 1H-indole (1 g, 8.54 mmol) and 4-iodobenzoic acid (2.33 g, 9.40 mmol) in DMSO (20 mL) added $K_2CO_3$ (3.5 g, 25.6 mmol) at 25° C. The reaction mixture was saturated with argon for 10 minutes. CuI (324 mg, 1.70 mmol) and 8-hydroxyquinaldine (407 mg, 2.56 mmol) added to it and stirred at 90° C. for 24 hours. The reaction was monitored by TLC and LCMS. On completion of the reaction, it was diluted with water (100 mL) and acidified with 1.5 N HCl at 0° C. The resulted solids were filtered and washed with water to give 4-(1H-indol-1-yl)benzoic acid as brown solid that was used in next step without further purification.

Step 2. Preparation of Example 18

4-(1H-indol-1-yl)benzoic acid (350 mg, 1.47 mmol) and N,N-diisopropylethylamine (0.8 mL, 3.1 mmol) were stirred in DMF (10 mL). HATU (841 mg, 2.21 mmol) was added to it at room temperature and stirred for 10 minutes. 4-(1H-imidazol-2-yl)piperidine hydrochloride (302 mg, 1.62 mmol) was then added and the mixture stirred for 16 hours at room temperature. The reaction was monitored by TLC and LCMS. On completion of the reaction, it was diluted with ethyl acetate (100 mL) and washed with water (2×50 mL). The organic portion was dried, concentrated and the residue purified by flash column chromatography (5% methanol in DCM) to give the title compound as white solid. 1H NMR (d6-DMSO, 400 MHz): δ ppm 7.73-7.60 (m, 7H), 7.25-7.14 (m, 4H), 6.75 (d, 1H), 4.55 (bs, 1H), 3.95 (bs, 1H), 3.20-2.9 (m, 3H), 2.00 (bs, 2H), 1.90-1.65 (m, 2H). LC-MS (m/z): [M+H]=371.1.

Example 19. (4-(1H-imidazol-2-yl)piperidin-1-yl)(3'-(trifluoromethyl)-[1,1'-biphenyl]-4-yl)methanone (Scheme 7)

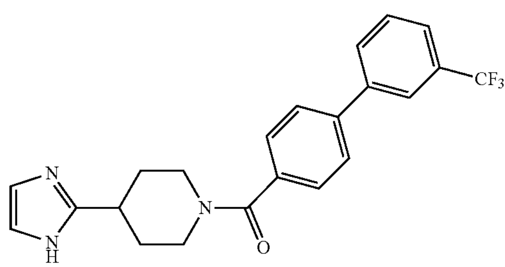 [SMILES: O=C(c1ccc(-c2cccc(C(F)(F)F)c2)cc1)N1CCC(c2ncc[nH]2)CC1]

This compound was synthesized in a similar manner to the procedure in Example 3, except that 3'-(trifluoromethyl)-[1,1'-biphenyl]-4-carboxylic acid was used instead of 4'-(trifluoromethyl)-[1,1'-biphenyl]-4-carboxylic acid. The compound was isolated as a trifluoroacetate salt. (4-(1H-imidazol-2-yl)piperidin-1-yl)(3'-(trifluoromethyl)-[1,1'-biphenyl]-4-yl)methanone 2,2,2-trifluoroacetate (4.73 mg) was dissolved in dichloromethane (1 mL) and washed with $NaHCO_3$ (1 mL, saturated, aqueous solution) before evaporating to give the free base. $^1$H NMR ($d_6$-DMSO, 400 MHz): δ ppm 11.98 (bs, 1H), 8.07-8.0 (m, 2H), 7.84 (d, 2H), 7.8-7.7 (m, 2H), 7.53 (d, 2H), 6.95 (s, 2H), 4.5 (bs, 1H), 3.7 (bs, 1H), 3.26-3.15 (m, 1H), 3.07-2.93 (m, 2H), 2.11-1.78 (m, 2H) 1.78-1.6 (m, 2H). LC-MS (m/z): [M+H]=400.1.

Example 20. (4-(1H-imidazol-2-yl)piperidin-1-yl)(4-(benzo[d][1,3]dioxol-4-yl)phenyl)methanone (Scheme 3)

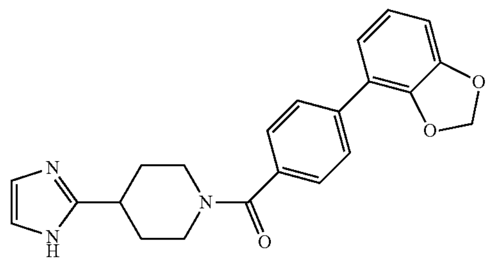 [SMILES: O=C(c1ccc(-c2cccc3c2OCO3)cc1)N1CCC(c2ncc[nH]2)CC1]

This compound was synthesized in a similar manner to the procedure in Example 2 (Step 1) except that 4-bromobenzo[d][1,3]dioxole was used instead of (3-bromophenyl)(methyl)-sulfane and there was no oxidation step. 1H NMR (d6-DMSO, 400 MHz): δ ppm 13.83 (bs, 1H), 7.83 (d, 2H), 7.55-7.45 (m, 4H), 7.22-7.15 (m, 1H), 6.95-7.05 (m, 2H), 6.1 (s, 2H), 4.6 (bs, 1H), 3.74 (bs, 1H), 2.96 (bs, 1H), 2.15-1.9 (m, 2H), 1.85-1.7 (m, 2H). LC-MS (m/z): [M+H]=376.2.

Example 21. (4-(1H-imidazol-2-yl)piperidin-1-yl)(1-phenyl-1H-indol-5-yl)methanone (Scheme 1)

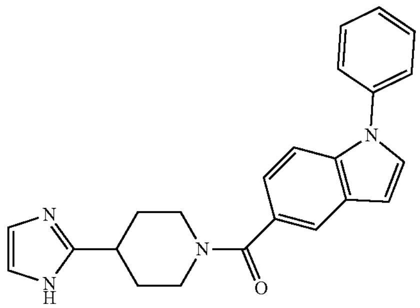 [SMILES: O=C(c1ccc2c(ccn2-c2ccccc2)c1)N1CCC(c2ncc[nH]2)CC1]

Step 1. Preparation of methyl 1-phenyl-1H-indole-5-carboxylate

To a stirred solution of methyl 1H-indole-5-carboxylate (0.5 g, 2.85 mmol) and iodobenzene (0.64 g, 3.14 mmol) in DMSO (10 mL) added $K_2CO_3$ (1.2 g, 8.57 mmol), CuI (0.011 g, 0.57 mmol) and 8-hydroxyquinaldine (0.136 g, 0.857 mmol) at 25° C. The reaction mixture stirred at 100° C. for 16 hours. The reaction was monitored by TLC and LCMS. On completion of the reaction, it was diluted with water (50 mL) and extracted with ethyl acetate (2×50 mL). The organic portion dried, concentrated and flash column purified (30% ethyl acetate in hexane) to give the title compound as brown liquid.

Step 2. Preparation of 1-phenyl-1H-indole-5-carboxylic acid

Methyl 1-phenyl-1H-indole-5-carboxylate (0.7 g, 2.78 mmol) in THF/methanol/$H_2O$ (6+2+2 mL) added lithium hydroxide monohydrate (0.35 g, 8.36 mmol) at 25° C. The reaction mixture stirred at 25° C. for 16 hours. The reaction was monitored by TLC and LCMS. On completion of the reaction, it was concentrated to get crude reaction mixture. The crude reaction mass was acidified with 1.5 N HCl (2 mL) at 0° C. The resulted solids were filtered and washed with water to give the title compound as white solid. The title compound used in next step without further purification.

Step 3. Preparation of Example 21

1-phenyl-1H-indole-5-carboxylic acid (200 mg, 0.84 mmol) and N,N-diisopropylethylamine (0.45 mL, 2.52 mmol) were stirred in DMF (10 mL). HATU (479 mg, 1.26 mmol) was added to it at room temperature and stirred for 10 minutes. 4-(1H-imidazol-2-yl)piperidine hydrochloride (190 mg, 1.08 mmol) was then added and the mixture stirred for 16 hours at room temperature. The reaction was monitored by TLC and LCMS. On completion of the reaction, it was diluted with ethyl acetate (100 mL) and washed with water (2×50 mL). The organic portion was dried, concentrated and the residue purified by flash column chromatography (5% methanol in DCM) to give the title compound as white solid. 1H NMR (d6-DMSO, 400 MHz): δ ppm 7.75-7.73 (m, 2H), 7.62-7.58 (m, 5H), 7.44-7.41 (m, 1H), 7.25 (dd, 1H), 7.08 (s, 2H), 6.77 (d, 1H), 4.31 (bs, 1H), 3.44 (bs, 1H), 3.10-2.90 (m, 3H), 1.91 (d, 2H), 1.76-1.65 (m, 2H). LC-MS (m/z): [M+H]=371.2.

Example 22. (4-(1H-imidazol-2-yl)piperidin-1-yl)(4-(5-(trifluoromethyl)thiophen-2-yl)phenyl)methanone (Scheme 3)

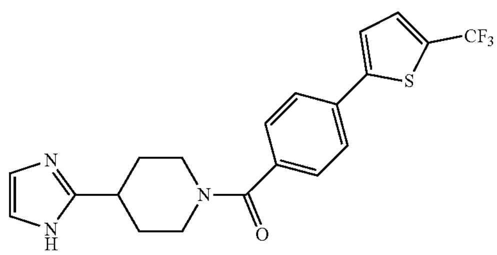 [SMILES: O=C(c1ccc(-c2ccc(C(F)(F)F)s2)cc1)N1CCC(c2ncc[nH]2)CC1]

This compound was synthesized in a similar manner to the procedure in Example 2 (Step 1), except that 2-bromo-5-(trifluoromethyl)thiophene was used instead of (3-bromophenyl)(methyl)sulfane and there was no oxidation step. 1H NMR (d6-DMSO, 400 MHz): δ ppm 13.92 (bs, 1H) 7.85 (d, 2H), 7.75 (d, 2H), 7.55 (d, 2H), 7.55-7.45 (m, 4H), 4.55 (bs, 1H), 3.70 (bs, 1H), 2.95 (bs, 1H), 2.15-1.85 (m, 2H), 1.85-1.65 (m, 2H). LC-MS (m/z): [M+H]=406.0.

Example 23. (4-(1H-imidazol-2-yl)piperidin-1-yl)(4-(1H-indol-3-yl)phenyl)methanone (Scheme 4)

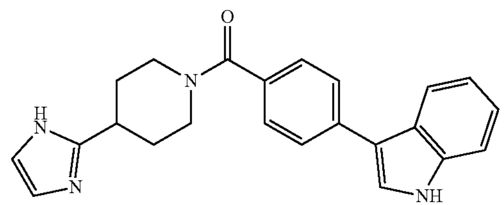 [SMILES: O=C(c1ccc(-c2c[nH]c3ccccc23)cc1)N1CCC(c2ncc[nH]2)CC1]

This compound was synthesized in a similar manner to the procedure in Example 5 (Step 3), except that 4-((1H-imidazol-2-yl)piperidine hydrochloride salt was used instead of 4-(5-methyl-1H-imidazol-2-yl)piperidine hydrochloride. 1H NMR (d6-DMSO), 400 MHz): δ ppm 11.73 (bs, 1H), 11.45 (s, 1H), 7.91 (d, 1H), 7.8-7.75 (m, 3H), 7.46 (d, 3H), 7.25-7.05 (m, 2H), 6.89 (s, 2H), 4.41 (bs, 1H), 3.92 (bs, 1H), 3.25-2.9 (m, 3H), 2.0-1.85 (m, 2H), 1.8-1.6 (m, 2H). LC-MS (m/z): [M+H]=371.2.

Example 24. (4-(1H-imidazol-2-yl)piperidin-1-yl)(4-(1H-indazol-3-yl)phenyl)methanone (Scheme 4)

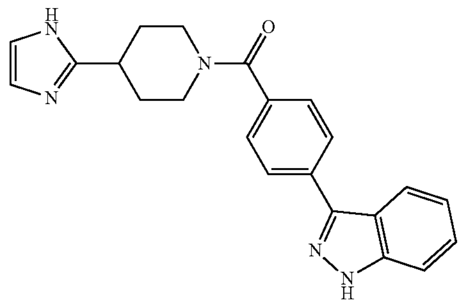 [SMILES: O=C(c1ccc(-c2n[nH]c3ccccc23)cc1)N1CCC(c2ncc[nH]2)CC1]

This compound was synthesized in a similar manner to the procedure in Example 6 (Step 3), except that 4-((1H-imidazol-2-yl)piperidine hydrochloride salt was used instead of 4-(5-methyl-1H-imidazol-2-yl)piperidine hydrochloride. 1H NMR (d6-DMSO), 400 MHz): δ ppm 13.35 (s, 1H), 8.15-8.05 (m, 3H), 7.61 (d, 1H), 7.55 (d, 2H), 7.42 (t, 1H), 7.23 (t, 1H), 7.00 (s, 2H), 4.51 (bs, 1H), 3.78 (bs, 1H), 3.1-2.9 (m, 3H), 2.1-1.85 (m, 2H), 1.8-1.6 (m, 2H). LC-MS (m/z): [M+H]=372.2.

Example 25. (4-((1H-imidazol-2-yl)methyl)piperidin-1-yl)(4'-(difluoromethyl)-[1,1'-biphenyl]-4-yl) methanone

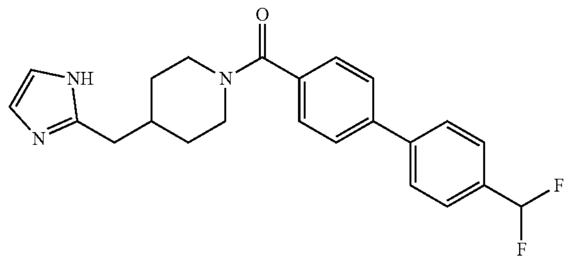 [SMILES: O=C(c1ccc(-c2ccc(C(F)F)cc2)cc1)N1CCC(Cc2ncc[nH]2)CC1]

This compound was synthesized in a similar manner to the procedure in Example 2 (Step 1), except that 1-bromo-4-(difluoromethyl)benzene was used instead of (3-bromophenyl)(methyl)sulfane, that 4-((1H-imidazol-2-yl)methyl) piperidine hydrochloride salt was used instead of 4-((1H-imidazol-2-yl)piperidine hydrochloride salt and there was no oxidation step. 1H NMR (d6-DMSO, 400 MHz at 100° C.): δ ppm 7.82 (d, 2H), 7.75 (d, 2H), 7.66 (d, 2H), 7.47 (d, 2H), 7.16-6.88 (m, 4H), 4.06-4.03 (m, 2H), 2.64 (d, 3H), 2.06-2.04 (m, 1H), 1.69 (d, 2H), 1.28-1.22 (m, 3H). LC-MS (m/z): [M+H]=396.2.

Example 26. (4-(4-methyl-1H-imidazol-2-yl)piperidin-1-yl)(4-(2-methyl-1H-indol-3-yl)phenyl)methanone

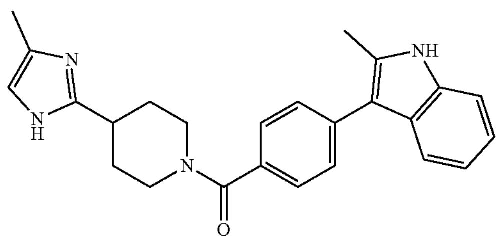 [SMILES: Cc1c[nH]c(C2CCN(C(=O)c3ccc(-c4c(C)[nH]c5ccccc45)cc3)CC2)n1]

Step 1. Preparation of 3-bromo-2-methyl-1H-indole

To a stirred solution of 2-methyl-1H-indole (5 g, 16.84 mmol) in THF (50 mL) was added N-bromo succinimide (3.15 g, 17.68 mmol) portion wise at 0° C. Resulting reaction mixture was stirred at room temperature for 3 hours. After completion, reaction mixture was quenched with cold water (100 mL) and extracted with ethyl acetate (2×200 mL). Combined organic layer was washed with brine, dried over sodium sulphate, filtered and concentrated under reduced pressure. Crude mass was purified by flash column chromatography (5-10% ethyl acetate in hexane) to get 3-bromo-2-methyl-1H-indole as white solid.

Step 2. Preparation of tert-butyl 3-bromo-2-methyl-1H-indole-1-carboxylate

To a stirred solution of 3-bromo-2-methyl-1H-indole (2 g, 9.52 mol) in DCM (30 mL) was added di-tert-butyl dicarbonate (2.84 mL, 12.38 mmol), DIPEA (3.31 mL, 19.05 mmol), followed by DMAP (233 mg, 1.91 mmol) at 0° C. Resulting reaction mixture was stirred at room temperature for 4 hours. After completion, reaction mixture was concentrated under reduced pressure, diluted with water (100 mL) and extracted with ethyl acetate (2×200 mL). Combined organic layer was washed with brine, dried over sodium sulphate, filtered and concentrated under reduced pressure. Crude material was purified by flash column chromatography (5-10% ethyl acetate in hexane) to get tert-butyl 3-bromo-2-methyl-1H-indole-1-carboxylate as white solid.

Step 3. Preparation of tert-butyl 2-methyl-3-(4,4,5,5-tetramethyl-1,3,2-dioxaborolan-2-yl)-1H-indole-1-carboxylate To a stirred solution of tert-butyl 3-bromo-2-methyl-indole-1-carboxylate (1 g, 3.23 mol) in dioxane (30 mL) bis pinacolatodiboron (1.23 g, 4.84 mmol) and potassium acetate (950 mg, 9.68 mmol) was added. Reaction mixture was degassed with argon for 10 min and $Pd(PPh_3)_2Cl_2$ (240 mg, 0.32 mmol) was added. Resulting mixture was heated at 100° C. for 16 hours. After completion, reaction mixture was filtered through a short pad of celite, diluted with water (100 mL) and extracted with ethyl acetate (2×100 mL). Combined organic layer was washed with brine, dried over sodium sulphate, filtered and concentrated under reduced pressure. Crude compound was purified by flash column chromatography (5-10% ethyl acetate in hexane) to give tert-butyl 2-methyl-3-(4,4,5,5-tetramethyl-1,3,2-dioxaborolan-2-yl)-1H-indole-1-carboxylate as white solid.

Step 4. Preparation of tert-butyl 2-methyl-3-(4-{[4-(4-methyl-1H-imidazol-2-yl)piperidin-1-yl]carbonyl}phenyl)-1H-indole-1-carboxylate To a stirred solution of (4-bromophenyl)-[4-(4-methyl-1H-imidazol-2-yl)-1-piperidyl]methanone (200.0 mg, 0.58 mmol) in 2-methyl tetrahydrofuran (5 mL) and water (0.5 mL) tert-butyl 2-methyl-3-(4,4,5,5-tetramethyl-1,3,2-dioxaborolan-2-yl)indole-1-carboxylate (246.21 mg, 0.69 mmol) and potassium carbonate (238.28 mg, 1.72 mmol) were added. Reaction mixture was degassed with argon for 10 min and $Pd(PPh_3)_2Cl_2$ (36.31 mg, 0.05 mmol) was added. Resulting mixture was heated at 85° C. for 16 hours. After completion, reaction mixture was filtered through a short pad of celite, diluted with water (100 mL) and extracted with ethyl acetate (2×100 mL). Combined organic layer was washed with brine, dried over sodium sulphate, filtered and concentrated under reduced pressure. Crude compound was purified by flash column chromatography (20-40% ethyl acetate in hexane) to give tert-butyl 2-methyl-3-(4-{[4-(4-methyl-1H-imidazol-2-yl)piperidin-1-yl]carbonyl}phenyl)-1H-indole-1-carboxylate as an off-white solid.

Step 5. Preparation of Example 26

To a stirred solution of tert-butyl 2-methyl-3-(4-{[4-(4-methyl-1H-imidazol-2-yl)piperidin-1-yl]carbonyl}phenyl)-1H-indole-1-carboxylate (100.0 mg, 0.20 mmol) in DCM (2 mL) was added HCl in dioxane (4M, 2 mL, 8 mmol) at 0° C. Resulting mixture was stirred at room temperature for 6 hours. After completion, reaction mixture was concentrated under reduced pressure, diluted with water, washed with sodium bicarobonate solution and extracted with 10% methanol in dichloromethane (2×50 mL). Combined organic layer was washed with brine, dried over sodium sulphate, filtered and concentrated under reduced pressure. Crude compound was purified by flash column chromatography (2-5% methanol in dichloromethane) to give (4-(4-methyl-1H-imidazol-2-yl)piperidin-1-yl)(4-(2-methyl-1H-indol-3-yl)phenyl)methanone as white solid. 1H NMR (d6-DMSO, 400 MHz at 100° C.): δ ppm 11.08 (bs, 1H), 10.89 (bs, 1H), 7.57-7.54 (m, 3H), 7.48 (d, 2H), 7.35 (d, 1H), 7.10-6.99 (m, 2H), 6.54 (bs, 1H), 4.13 (d, 2H), 3.19-3.12 (m, 2H), 2.98-2.94 (m, 1H), 2.49 (s, 3H), 2.11 (s, 3H), 1.97-1.92 (m, 2H), 1.79-1.69 (m, 2H). LC-MS (m/z): [M+H]=399.2.

Example 27. (4-(1H-indol-6-yl)phenyl)(4-(5-methyl-1H-imidazol-2-yl)piperidin-1-yl)methanone

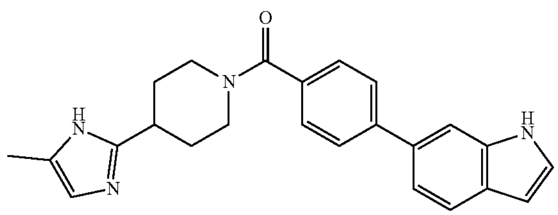 [SMILES: Cc1cnc(C2CCN(C(=O)c3ccc(-c4ccc5cc[nH]c5c4)cc3)CC2)[nH]1]

Step 1. Preparation of 4-(4-methyl-1H-imidazol-2-yl)-1-{[4-(4,4,5,5-tetramethyl-1,3,2-dioxaborolan-2-yl)phenyl]carbonyl}piperidine To a stirred solution of 1-[(4-bromophenyl)carbonyl]-4-(5-methyl-1H-imidazol-2-yl)piperidine (3.5 g, 10.05 mmol) in dioxane (30 mL) bis pinacolatodiboron (3.83 g, 15.07 mmol) and potassium acetate (2.96 g, 30.15 mmol) were added. It was degassed with argon for 10 min and $Pd(PPh_3)_2Cl_2$ (705 mg, 1.01 mmol) was added. Resulting mixture was heated at 90° C. for 16 hours. After completion, reaction mixture was filtered through a short pad of celite, diluted with water (100 mL) and extracted with ethyl acetate (2×100 mL). Combined organic layer was washed with brine, dried over sodium sulphate, filtered and concentrated under reduced pressure. Crude compound was purified by flash column chromatography (5-10% methanol in dichloromethane) to give 4-(4-methyl-1H-imidazol-2-yl)-1-{[4-(4,4,5,5-tetramethyl-1,3,2-dioxaborolan-2-yl)phenyl]carbonyl}piperidine as brown solid.

Step 2. Preparation of Example 27

To a stirred solution of 6-bromo-1H-indole (100.0 mg, 0.51 mmol) in 2-methyl tetrahydrofuran (6 mL) and water (2 mL) [4-(4-methyl-1H-imidazol-2-yl)-1-piperidyl]-[4-(4,4,5,5-tetramethyl-1,3,2-dioxaborolan-2-yl)phenyl]methanone (241.84 mg 0.61 mmol) and potassium carbonate (211.53 mg, 1.53 mmol) were added. It was degassed with argon for 10 min and $PdCl_2(PPh_3)_2$ (35.81 mg, 0.05 mmol) was added. Resulting mixture was heated at 80° C. for 10 hours. After completion, reaction mixture was filtered through a short pad of celite, diluted with water (100 mL) and extracted with ethyl acetate (2×100 mL). Combined organic layer was washed with brine, dried over sodium sulphate, filtered and concentrated under reduced pressure. Crude compound was purified by column chromatography (2-5% methanol in dichloromethane) to afford (4-(1H-indol-6-yl)phenyl)(4-(5-methyl-1H-imidazol-2-yl)piperidin-1-yl)methanone as white solid. 1H NMR (d6-DMSO, 400 MHz at 100° C.): δ ppm 11.10 (bs, 1H), 10.87 (bs, 1H), 7.72 (t, 3H), 7.63 (d, 1H), 7.47 (d, 2H), 7.34 (d, 2H), 6.62 (bs, 1H), 6.46 (bs, 1H), 4.10-4.06 (m, 2H), 3.14 (t, 2H), 2.97-2.95 (m, 1H), 2.15 (s, 3H), 1.96-1.93 (m, 2H), 1.74-1.72 (m, 2H). LC-MS (m/z): [M+H]=385.2.

Example 28. (4-(1H-imidazol-2-yl)piperidin-1-yl)(1H,1'H-[3,4'-biindol]-6-yl)methanone

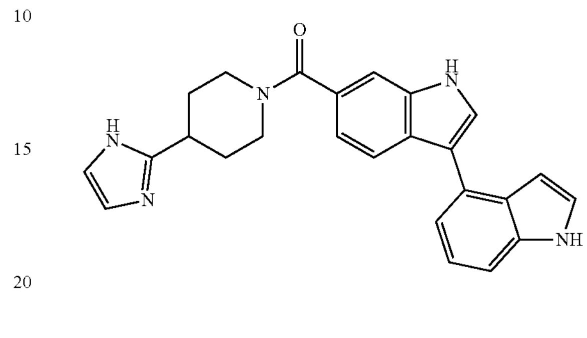

Step 1. Preparation of 3-bromo-6-{[4-(1H-imidazol-2-yl)piperidin-1-yl]carbonyl}-1H-indole To a stirred solution of 3-bromo-1H-indole-6-carboxylic acid (1 g, 4.19 mmol) in THF (20 mL) N,N-diisopropylethylamine (2.16 mL, 12.56 mmol) and HATU (2.07 g, 5.44 mmol) were added and stirred for 10 min. 4-(1H-imidazol-2-yl)piperidine (759 mg, 5.02 mmol) was added and resulting mixture was stirred at room temperature for 16 hours. After completion, reaction mixture was diluted with water (100 mL) and extracted with 10% methanol in DCM (2×50 mL). Combined organic layer was washed with brine, dried over sodium sulphate, filtered and concentrated under reduced pressure. Crude material was purified by flash column chromatography (2-5% methanol in DCM) to get 3-bromo-6-{[4-(1H-imidazol-2-yl)piperidin-1-yl]carbonyl}-1H-indole as white solid.

Step 2. Preparation of Example 28

To a stirred solution of 3-bromo-6-{[4-(1H-imidazol-2-yl)piperidin-1-yl]carbonyl}-1H-indole (300.0 mg, 0.81 mmol) and 1H-indol-4-ylboronic acid (168.84 mg, 1.05 mmol) in dioxane (2.5 mL), DMF (0.5 mL) and water (0.5 mL) sodium carbonate (256.39 mg, 2.42 mmol) was added. It was degassed with argon for 10 min and $PdCl_2(dppf)$ (59 mg, 0.08 mmol) was added. Resulting mixture was heated under microwave irradiation at 100° C. for 1 hour. After completion, volatiles were removed under reduced pressure, diluted with water (50 mL) and extracted with 10% methanol in dichloromethane (2×50 mL). Combined organic layer was washed with brine, dried over Na2SO4, filtered and concentrated under reduced pressure. Crude compound was purified by flash column chromatography (2-5% methanol in dichloromethane) followed by preparative HPLC to give [4-(1H-imidazol-2-yl)-1-piperidyl]-[3-(1H-indol-4-yl)-1H-indol-6-yl]methanone as white solid. 1H NMR (d6-DMSO, 400 MHz at 100° C.): δ ppm 11.38 (bs, 1H), 11.17 (bs, 1H), 10.82 (bs, 1H), 7.74 (d, 1H), 7.69 (s, 1H), 7.55 (s, 1H), 7.36 (d, 1H), 7.31 (t, 1H), 7.23 (d, 1H), 7.17 (t, 1H), 7.11 (d, 1H), 6.95 (bs, 1H), 6.78 (bs, 1H), 6.56-6.53 (m, 1H), 4.18-4.14 (m, 2H), 3.19-3.13 (m, 2H), 3.04-2.98 (m, 1H), 1.99-1.95 (m, 2H), 1.81-1.75 (m, 2H). LC-MS (m/z): [M+H]=410.2.

Example 29. [4-(1H-imidazol-2-yl)-1-piperidyl]-[3-(1H-indol-3-yl)-1H-indol-6-yl]methanone

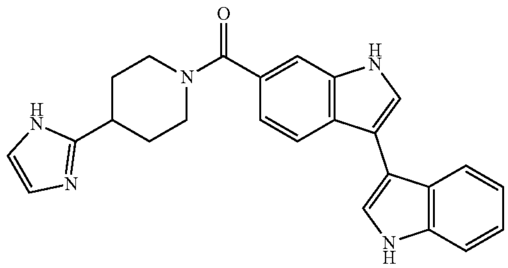 [SMILES: O=C(c1ccc2c(-c3c[nH]c4ccccc34)c[nH]c2c1)N1CCC(c2ncc[nH]2)CC1]

To a stirred solution of 3-bromo-6-{[4-(1H-imidazol-2-yl)piperidin-1-yl]carbonyl}-1H-indole (400.0 mg, 1.08 mmol) and (1-tert-butoxycarbonylindol-3-yl)boronic acid (364.90 mg, 1.40 mmol) in dioxane (3 mL), DMF (0.5 mL) and water (0.5 mL) sodium carbonate (341.86 mg, 3.23 mmol) was added. The mixture was degassed with argon for 10 min and $PdCl_2$(dppf) (78.67 mg, 0.11 mmol) was added. Resulting mixture was heated under microwave irradiation at 100° C. for 1 hour After completion, volatiles were removed under reduced pressure, diluted with water (50 mL) and extracted with 10% methanol in dichloromethane (2×50 mL). Combined organic layer was washed with brine, dried over $Na_2SO_4$, filtered and concentrated under reduced pressure. Crude compound was purified by flash column chromatography (3-7% methanol in DCM) followed by preparative HPLC to give [4-(1H-imidazol-2-yl)-1-piperidyl]-[3-(1H-indol-3-yl)-1H-indol-6-yl]methanone as white solid. 1H NMR (d6-DMSO, 400 MHz at 100° C.): 5 ppm 11.40 (bs, 1H), 11.02 (bs, 1H), 10.84 (bs, 1H), 7.78-7.73 (m, 2H), 7.66 (bs, 1H), 7.57 (bs, 1H), 7.52 (s, 1H), 7.46 (d, 1H), 7.17-7.04 (m, 3H), 6.94 (bs, 1H), 6.79 (bs, 1H), 4.18-4.15 (m, 2H), 3.15 (t, 2H), 3.04-2.99 (m, 1H), 1.98-1.94 (m, 2H), 1.81-1.75 (m, 2H). LC-MS (m/z): [M+H]=410.2.

Example 30. (4-(1H-imidazol-2-yl)piperidin-1-yl)(4-(1H-indol-2-yl)phenyl)methanone (Scheme 6)

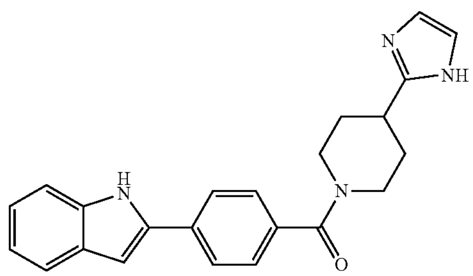 [SMILES: O=C(c1ccc(-c2cc3ccccc3[nH]2)cc1)N1CCC(c2ncc[nH]2)CC1]

This compound was synthesized in a similar manner to the procedure in Example 17 (Step 2) except that (1-(tert-butoxycarbonyl)-1H-indol-2-yl)boronic acid was used instead of 4-(4,4,5,5-tetramethyl-1,3,2-dioxaborolan-2-yl)-1H-indole. The final compound was prepared using the HCl mediated deprotection step (below).

To a stirred solution of tert-butyl 2-(4-(4-(1H-imidazol-2-yl)piperidine-1-carbonyl)phenyl)-1H-indole-1-carboxylate (0.1 g, 0.21 mmol) in dry DCM (5 mL), HCl in 1,4 dioxane 4M (5 mL) was added dropwise at 0° C. and the reaction mixture was stirred at RT for 2 hours. After completion of the reaction, the reaction mixture was concentrated under vacuum. The resulting crude residue was purified by preparative HPLC to give (4-(1H-imidazol-2-yl)piperidin-1-yl)(4-(1H-indol-2-yl)phenyl)methanone as a brown solid. 1H NMR (d6-DMSO, 400 MHz at 100° C.): δ ppm 7.94 (d, 2H), 7.56 (d, 1H), 7.50 (d, 2H), 7.42 (d, 1H), 7.13 (t, 1H), 6.95-7.05 (m, 3H), 6.78 (bs, 1H), 4.44 (bs, 1H), 3.74 (bs, 1H), 3.15-3.30 (m, 1H), 2.9-3.1 (m, 2H), 1.8-2.1 (m, 2H), 1.6-1.8 (m, 2H). LC-MS (m/z): [M+H]=371.1.

Example 31. (4-(5-methyl-1H-imidazol-2-yl)piperidin-1-yl)(3-phenyl-1H-indol-6-yl)methanone

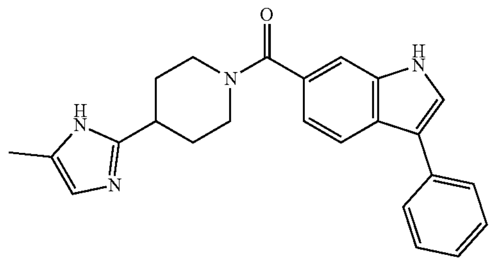 [SMILES: Cc1cnc(C2CCN(C(=O)c3ccc4c(-c5ccccc5)c[nH]c4c3)CC2)[nH]1]

Step 1. Preparation of 3-bromo-6-{[4-(5-methyl-1H-imidazol-2-yl)piperidin-1-yl]carbonyl}-1H-indole To a stirred solution of 3-bromo-1H-indole-6-carboxylic acid (1 g, 4.19 mmol) in THF (20 mL) N,N-diisopropylethylamine (2.16 mL, 12.56 mmol) and HATU (2.07 g, 5.44 mmol) were added and stirred for 10 min. 4-(5-methyl-1H-imidazol-2-yl)piperidine (829 mg, 5.02 mmol) was added and resulting mixture was stirred at room temperature for 16 hours. After completion, reaction mixture was diluted with water (100 mL) and extracted with 10% methanol in dichloromethane (2×50 mL). Combined organic layer was washed with brine, dried over sodium sulphate, filtered and concentrated under reduced pressure. Crude material was purified by flash column chromatography (2-5% methanol in dichloromethane) to get 3-bromo-6-{[4-(5-methyl-1H-imidazol-2-yl)piperidin-1-yl]carbonyl}-1H-indole as white solid.

Step 2. Preparation of Example 31

To a stirred solution of 3-bromo-6-{[4-(5-methyl-1H-imidazol-2-yl)piperidin-1-yl]carbonyl}-1H-indole (250.0 mg, 0.65 mmol), and phenylboronic acid (102.74 mg, 0.84 mmol) in dioxane (2.5 mL), DMF (0.5 mL) and water (0.5 mL) sodium carbonate (205.90 mg, 1.94 mmol) was added. The mixture was degassed with argon for 10 min and $PdCl_2$(dppf) (47.38 mg, 0.07 mmol) was added. Resulting mixture was heated under microwave irradiation at 100° C. for 1 hour. After completion, the volatiles were removed under reduced pressure, diluted with water (50 mL) and extracted with ethyl acetate (2×50 mL). Combined organic layer was washed with brine, dried over sodium sulphate, filtered and concentrated under reduced pressure. Crude compound was purified by flash column chromatography (2-5% methanol in dichloromethane) followed by preparative HPLC to give the title compound as white solid. 1H NMR (d6-DMSO, 400 MHz at 20° C.): δ ppm 11.55 (bs, 1H), 11.48 (bs, 1H), 7.89 (d, 1H), 7.81 (s, 1H), 7.69 (d, 2H), 7.50 (s, 1H), 7.44 (t, 2H), 7.25 (t, 1H), 7.13 (d, 1H), 6.66-6.40 (bs, 1H), 3.98-3.88 (m, 1H), 3.08-3.02 (m, 2H), 2.89-2.80 (m, 2H), 2.08 (s, 3H), 1.91-1.85 (m, 2H), 1.70-1.64 (m, 2H). LC-MS (m/z): [M+H]=385.2.

Example 32. (4-(1H-imidazol-2-yl)piperidin-1-yl)(3-phenyl-1H-indol-6-yl)methanone

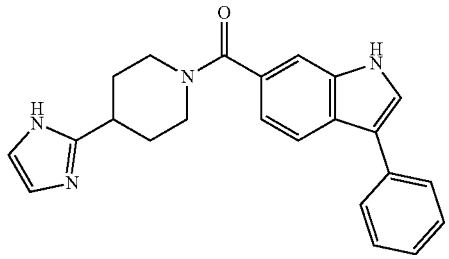 [SMILES: O=C(c1ccc2c(-c3ccccc3)c[nH]c2c1)N1CCC(c2ncc[nH]2)CC1]

This compound was prepared in a similar fashion to Example 31, except that 4-((1H-imidazol-2-yl)piperidine hydrochloride salt was used instead of 4-(5-methyl-1H-imidazol-2-yl)piperidine in Step 1. 1 H NMR (d6-DMSO, 400 MHz at 100° C.): δ ppm 11.38 (bs, 1H), 11.20 (bs, 1H), 7.88 (d, 1H), 7.70-7.68 (m, 3H), 7.53 (s, 1H), 7.44 (t, 2H), 7.25 (t, 1H), 7.18-7.14 (m, 1H), 6.86 (bs, 2H), 4.16-4.13 (m, 2H), 3.15 (t, 2H), 3.02-3.00 (m, 1H), 1.98-1.94 (m, 2H), 1.81-1.75 (m, 2H). LC-MS (m/z): [M+H]=371.2

Example 33. (4-((1H-imidazol-2-yl)amino)piperidin-1-yl)(4'-(difluoromethyl)-[1,1'-biphenyl]-4-yl)methanone (Scheme 2)

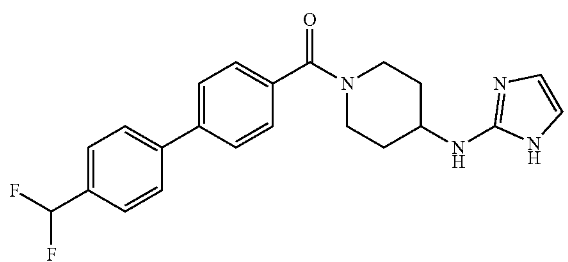 [SMILES: O=C(c1ccc(-c2ccc(C(F)F)cc2)cc1)N1CCC(Nc2ncc[nH]2)CC1]

This was prepared in a similar manner to Example 1 except that 4-[4-(difluoromethyl)phenyl]benzoic acid was used instead of 4'-fluoro-[1,1'-biphenyl]-4-carboxylic acid in step 3 to afford 1-({4-[4-(difluoromethyl)phenyl]phenyl}carbonyl)-N-(1H-imidazol-2-yl)piperidin-4-amine as white solid. 1H NMR (d6-DMSO, 400 MHz at 100° C.): δ ppm 8.14 (bs, 1H), 7.83 (d, 2H), 7.76 (d, 2H), 7.67 (d, 2H), 7.50 (d, 2H), 7.16-6.88 (m, 1H), 6.54 (s, 2H), 5.51-5.49 (m, 1H), 4.00-3.96 (m, 2H), 3.73-3.69 (m, 1H), 3.21-3.11 (m, 2H), 2.00-1.91 (m, 2H), 1.52-1.44 (m, 2H). LC-MS (m/z): [M+H]=397.2.

Example 34. (4-(5-fluoro-1H-indol-3-yl)phenyl)(4-(4-methyl-1H-imidazol-2-yl)piperidin-1-yl)methanone

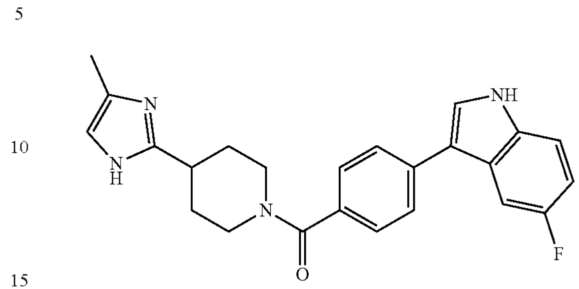

Step 1. Preparation of 5-fluoro-3-(4-{[4-(4-methyl-1H-imidazol-2-yl)piperidin-1-yl]carbonyl}phenyl)-1-[(4-methylbenzene)sulfonyl]-1H-indole To a stirred solution of 3-bromo-5-fluoro-1-tosyl-1H-indole (600.0 mg, 1.63 mmol) in 2-methyl tetrahydrofuran (15 mL) and water (5 mL), 4-(4-methyl-1H-imidazol-2-yl)-1-{[4-(4,4,5,5-tetramethyl-1,3,2-dioxaborolan-2-yl)phenyl]carbonyl}piperidine (772.81 mg, 1.96 mmol) and potassium carbonate (675.57 mg, 4.89 mmol) were added. Reaction mixture was degassed with argon for 10 minutes and $Pd(PPh_3)_2Cl_2$ (35.81 mg, 0.05 mmol) was added. Resulting mixture was heated at 85° C. for 16 hours. After completion, reaction mixture was filtered through a short pad of celite, diluted with water (100 mL) and extracted with ethyl acetate (2×100 mL). Combined organic layer was washed with brine, dried over sodium sulphate, filtered and concentrated under reduced pressure. Crude compound was purified by flash column chromatography (5-10% methanol in dichloromethane) to give 5-fluoro-3-(4-{[4-(4-methyl-1H-imidazol-2-yl)piperidin-1-yl]carbonyl}phenyl)-1-[(4-methylbenzene)sulfonyl]-1H-indole as brown solid.

Step 2. Preparation of Example 34

To a stirred solution of 5-fluoro-3-(4-{[4-(4-methyl-1H-imidazol-2-yl)piperidin-1-yl]carbonyl}phenyl)-1-[(4-methylbenzene)sulfonyl]-1H-indole (200.0 mg, 0.75 mmol) in methanol:THF (12 mL; 1:1) 4 M NaOH (0.45 mL, 1.8 mmol) was added drop wise at 0° C. Reaction mixture was slowly warmed to room temperature and stirred for 4 hours. After completion, it was diluted with water (30 mL) and extracted with ethyl acetate (2×50 mL). Combined organic layer was washed with brine, dried over sodium sulphate, filtered and concentrated under reduced pressure. Crude compound was purified by column chromatography (2-5% methanol in dichloromethane) to give 5-fluoro-3-(4-{[4-(4-methyl-1H-imidazol-2-yl)piperidin-1-yl]carbonyl}phenyl)-1H-indole as an off-white solid. 1H NMR (d6-DMSO, 400 MHz at 100° C.): δ ppm 11.23 (bs, 2H), 7.76 (s, 1H), 7.72 (d, 2H), 7.57 (d, 1H), 7.48-7.45 (t, 2H), 6.99 (t, 1H), 6.53 (bs, 2H), 4.11 (d, 2H), 3.15 (t, 2H), 2.85-2.80 (m, 1H), 2.11 (s, 3H), 1.97-1.93 (m, 2H), 1.77-1.69 (m, 2H). LC-MS (m/z): [M+H]=403.2.

Comparator Analogs (CA-#)

In a comparative assessment, receptor affinities ($IC_{50}$) for serotonin 5-HT2B and hERG were compared against the compounds of the invention; respective inhibitory data for the compounds of the invention and the comparators are presented in Table 2. The half (50%) maximal inhibitory concentration ($IC_{50}$) is the measure of potency of a compound in inhibiting a specific biological function, i.e., the receptors. Some of the comparators were previously described in WO2010/080357; as can be observed, minor changes in the core molecule, for example: a) changing the methylene linker in CA-1 to an amine in Ex-1; b) displaced (meta) sulfonylmethyl (Ex-2) in lieu of para-fluorine (CA-4) or para-cyano (CA-5); c) $CF_3$ (Ex-3) in lieu of fluorine (CA-4) or cyano (CA-5); and d) displaced meta-chlorine (Ex-10) in lieu of para-fluorine (CA-4); provided unpredicted results in inhibitory activity of 5-HT2B and/or hERG. A comparative table that differentiates the Examples of the invention from the comparator analogs is provided in Table 1 for some of the compounds of the invention. The comparator analogs (CA-1 to CA-7) are shown below.

CA-1. (4-((1H-imidazol-2-yl)methyl)piperidin-1-yl)(4'-fluoro-[1,1'-biphenyl]-4-yl)methanone

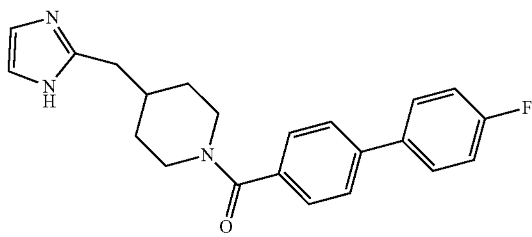 [SMILES: O=C(c1ccc(-c2ccc(F)cc2)cc1)N1CCC(Cc2ncc[nH]2)CC1]

CA-2. (4-(1H-benzo[d]imidazol-2-yl)piperidin-1-yl)(4'-(trifluoromethoxy)-[1,1'-biphenyl]-4-yl)methanone, described in WO2010/080357 (Example 37)

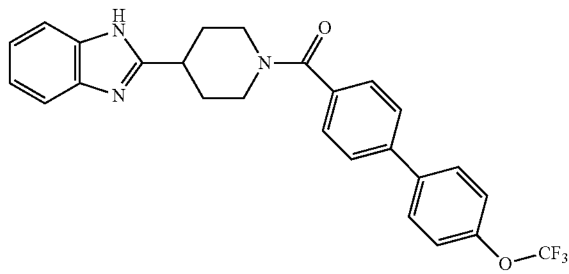 [SMILES: O=C(c1ccc(-c2ccc(OC(F)(F)F)cc2)cc1)N1CCC(c2nc3ccccc3[nH]2)CC1]

CA-3. (4-(1H-imidazol-2-yl)piperidin-1-yl)([1,1'-biphenyl]-4-yl)methanone, described in WO2010/080357 (Example 39)

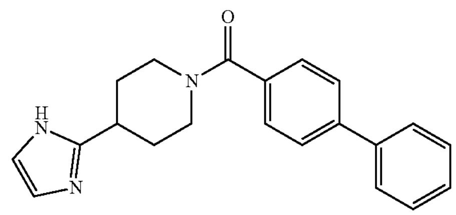

CA-4. (4-(1H-imidazol-2-yl)piperidin-1-yl)(4'-fluoro-[1,1'-biphenyl]-4-yl)methanone, described in WO2010/080357 (Example 54)

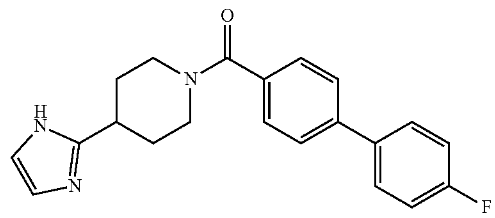 [SMILES: O=C(c1ccc(-c2ccc(F)cc2)cc1)N1CCC(c2ncc[nH]2)CC1]

CA-5. 4'-(4-(1H-imidazol-2-yl)piperidine-1-carbonyl)-[1,1'-biphenyl]-4-carbonitrile

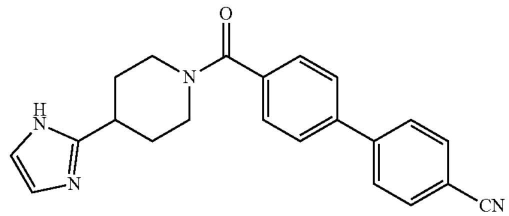 [SMILES: N#Cc1ccc(-c2ccc(C(=O)N3CCC(c4ncc[nH]4)CC3)cc2)cc1]

CA-6. (4'-fluoro-[1,1'-biphenyl]-4-yl)(4-(4-methyl-1H-imidazol-2-yl)piperidin-1-yl)methanone

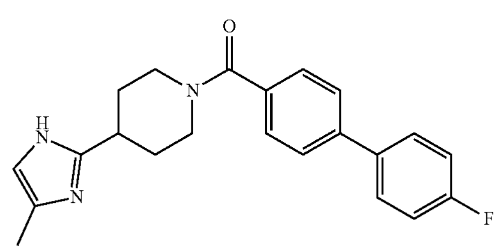 [SMILES: Cc1c[nH]c(C2CCN(C(=O)c3ccc(-c4ccc(F)cc4)cc3)CC2)n1]

CA-7. (4-(1H-imidazol-2-yl)piperidin-1-yl)(2'-fluoro-[1,1'-biphenyl]-4-yl)methanone

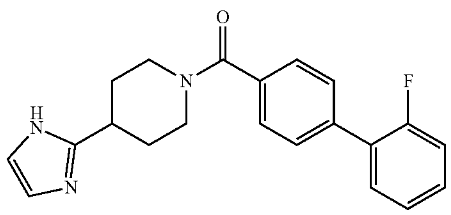 [SMILES: O=C(c1ccc(-c2ccccc2F)cc1)N1CCC(c2ncc[nH]2)CC1]

TABLE 1

| Differentiation of Invention Examples vs Comparator Analog(s) | |
|---|---|
| Example # | Comparator Analog (CA #) |
| 1 | 1, 4, 7 |
| 2 | 3, 4, 5 |
| 3 | 3, 4, 5 |
| 4 | 6 |
| 5 | 6 |
| 6 | 6 |
| 7 | 1, 4 |
| 8 | 3 |
| 9 | 1, 3 |
| 10 | 3, 4, 5, 7 |
| 11 | 3 |
| 12 | 1 |
| 13 | — |
| 14 | — |
| 15 | 3 |
| 16 | 3, 4, 5 |
| 17 | — |
| 18 | — |
| 19 | 4, 5, 7 |
| 20 | — |
| 21 | — |
| 22 | 3, 4, 5 |
| 23 | 3, 4 |
| 24 | 3, 4 |
| 25 | 1 |
| 26 | — |
| 27 | — |
| 28 | — |
| 29 | — |
| 30 | — |
| 31 | — |
| 32 | — |
| 33 | 1, 4 |
| 34 | — |

Canine 5-HT2B (c5-HT2B) In-Vitro Assay

CHO-K1 cells stably expressing the canine 5-HT2B receptor were seeded at 20,000 cells per well in 20 μl culture media (DMEM with GlutaMAX™ high glucose+5% dialyzed FBS+10 mM HEPES+1×MEM Non-Essential Amino Acids of a 384-well black plate with clear bottom for at least 18 hours at 37° C. and 5% $CO_2$. The cell plate was loaded with 20 μl/well of the FLIPR® Calcium 5 Assay kit prepared in HBSS containing calcium and magnesium supplemented with 20 mM HEPES and 5 mM Probenecid at pH 7.4 and incubated at 37° C. and 5% $CO_2$ for 30 minutes and then an additional 30 minutes at room temperature. The intracellular calcium response was measured using the FLIPR Tetra® instrument measuring the kinetic response of the Calcium 5 dye at an excitation wavelength of 470-495 nm and emission wavelength of 515-575 nm at room temperature. The cells were initially challenged with a 5× concentration of the antagonist (10 μl/well) after an initial baseline recording and the calcium response was recorded for almost 2 minutes. After the completion of the initial antagonist challenge, the cell plate was incubated at room temperature in the FLIPR Tetra® instrument for 10 minutes. Finally, a second kinetic assay was performed after the 10 minute incubation at room temperature to measure the inhibitory response of the $EC_{80}$ concentration of serotonin (15 μl/well) after an initial baseline recording. The $IC_{50}$ concentration was determined for each antagonist tested.

hERG In-Vitro Assay

Stock solutions of compounds of the invention and positive control (cisapride; 0.001-3 μM) were prepared in DMSO. Stock solutions were diluted in a HEPES-buffered physiological saline solution. Test and control solutions contained 0.3% DMSO. Human hERG/HEK293 renal epithelial cells stably transfected with full length hERG cDNA were cultured in Dulbecco's Modified Eagle Medium/Nutrient Mixture F-12 (D-MEM/F-12) supplemented with 10% fetal bovine serum, 100 U/mL penicillin G sodium, 100 μg/mL streptomycin sulfate and 500 μg/mL G418. Before testing, cells in culture dishes were rinsed with Hank's Balanced Salt Solution (HBSS) and detached with accutase. Immediately before use in the IonWorks Barracuda™ system, the cells were washed with buffered physiological saline solution (HB-PS) buffer to remove the accutase and re-suspended in 5 mL of HB-PS. The test article effects were evaluated using IonWorks Barracuda™ systems (Molecular Devices Corporation, Union City, CA). HEPES-buffered intracellular solution for whole cell recordings was loaded into the intracellular compartment of the Population Patch Clamp™ (PPC) planar electrode.

Extracellular buffer (HB-PS) was loaded into PPC planar electrode plate wells (11 μL/well). The cell suspension was pipetted into the wells of the PPC planar electrode (9 μL/well). After establishment of a whole-cell configuration (the perforated patch), membrane currents were recorded using patch clamp amplifier in the IonWorks Barracuda™ system. The current recordings were performed one (1) time before test article application to the cells (baseline) and one (1) time after application of the test article. Test article concentrations were applied to naïve cells. Each application consisted of addition of 20 μL of 2× concentrated test article solution to the total 40 μL of final volume of the extracellular well of the PPC plate. Duration of exposure to each compound concentration was five (5) minutes. hERG current was elicited using a pulse pattern with fixed amplitudes (the first conditioning pre-pulse to 10 mV for 60 second, the second conditioning pre-pulse: −90 mV for 20 ms; the test pulse: +40 mV for 100 ms) from a holding potential of 0 mV ('zero holding' procedure). hERG current was measured as a difference between the peak current at 1 ms and at the end of test step to +40 mV. Data acquisition and analyses were performed using the IonWorks Barracuda™ system operation software (version 2.0.2). The decrease in current amplitude after test article application was used to calculate the percent block relative to control. Results for each test article concentration (n≥1) were averaged; the mean and standard deviation values were calculated and used to generate dose-response curves.

In accordance with the in-vitro assays described above, the $IC_{50}$ affinities for the c5-HT2B and hERG receptors for the compounds of the invention and comparator analogs are described in Table 2.

TABLE 2

| Compound Receptor $IC_{50}$ Affinities for c5-HT2B and hERG | | |
|---|---|---|
| Example | c5-HT2B (nM) | hERG (nM) |
| 1 | 2 | 1542 |
| 2 | 52.3 | 72350 |
| 3 | 5.1 | 3475 |
| 4 | 21.95 | 1128 |
| 5 | 0.33 | 6632 |
| 6 | 0.65 | 35461 |
| 7 | 30.2 | 2495 |

TABLE 2-continued

| Compound Receptor $IC_{50}$ Affinities for c5-HT2B and hERG | | |
|---|---|---|
| Example | c5-HT2B (nM) | hERG (nM) |
| 8 | 0.64 | 3144 |
| 9 | 0.42 | 3848 |
| 10 | 0.51 | 2767 |
| 11 | 4.5 | 3284 |
| 12 | 63.9 | 4839 |
| 13 | 1.4 | 1728 |
| 14 | 1.3 | 5724 |
| 15 | 0.65 | 2009 |
| 16 | 0.31 | 2736 |
| 17 | 0.04 | 5873 |
| 18 | 0.01 | 3400 |
| 19 | 0.89 | 1473 |
| 20 | 0.01 | 3394 |
| 21 | 3.1 | 4311 |
| 22 | 20.5 | 2798 |
| 23 | 0.02 | 24830 |
| 24 | 0.33 | 33550 |
| 25 | 0.46 | 3398 |
| 26 | 0.84 | 13121 |
| 27 | 1.1 | 9282 |
| 28 | 1.2 | >30000 |
| 29 | 1.4 | 27077 |
| 30 | 1.95 | 11037 |
| 31 | 4.5 | 19615 |
| 32 | 7.3 | 15228 |
| 33 | 18.6 | 5292 |
| 34 | 21 | 13908 |
| CA-1 | 0.3 | 546 |
| CA-2 | 95* | — |
| CA-3 | 0.64 | 611 |
| CA-4 | 0.08 | <30 |
| CA-5 | 453 | 54 |
| CA-6 | 7.3 | <30 |
| CA-7 | 0.09 | 1097 |

*Literature Value

As can be seen in Table 2, the compounds of the invention have a high affinity for the c5-HT2B receptor and a lower affinity for the hERG receptor when compared against similar chemical analogs. As described herein, preferred compounds are those with a lower (or no) affinity to hERG so as not to result in the potentially fatal LOTS disorder.

We claim:

1. A compound selected from the group consisting of:
(4-(1H-imidazol-2-yl)piperidin-1-yl)(4'-(trifluoromethyl)-[1,1'-biphenyl]-4-yl)methanone;
(4-(1H-imidazol-2-yl)piperidin-1-yl)(3'-chloro-[1,1'-biphenyl]-4-yl)methanone, trifluoroacetic acid salt; and
(4-(1H-imidazol-2-yl)piperidin-1-yl)(4'-(difluoromethyl)-[1,1'-biphenyl]-4-yl)methanone;
and veterinary acceptable salts thereof.

2. A compound of claim 1, that is
(4-(1H-imidazol-2-yl)piperidin-1-yl)(4'-(trifluoromethyl)-[1,1'-biphenyl]-4-yl)methanone or
(4-(1H-imidazol-2-yl)piperidin-1-yl)(4'-(difluoromethyl)-[1,1'-biphenyl]-4-yl)methanone;
and veterinary acceptable salts thereof.

3. A compound of claim 2, that is
(4-(1H-imidazol-2-yl)piperidin-1-yl)(4'-(difluoromethyl)-[1,1'-biphenyl]-4-yl)methanone;
and veterinary acceptable salts thereof.

4. A composition comprising a compound selected from the group consisting of:
(4-(1H-imidazol-2-yl)piperidin-1-yl)(4'-(trifluoromethyl)-[1,1'-biphenyl]-4-yl)methanone;
(4-(1H-imidazol-2-yl)piperidin-1-yl)(3'-chloro-[1,1'-biphenyl]-4-yl)methanone, trifluoroacetic acid salt; and
(4-(1H-imidazol-2-yl)piperidin-1-yl)(4'-(difluoromethyl)-[1,1'-biphenyl]-4-yl)methanone;
and a veterinary acceptable salt thereof.

5. A composition of claim 4, comprising a compound that is
(4-(1H-imidazol-2-yl)piperidin-1-yl)(4'-(difluoromethyl)-[1,1'-biphenyl]-4-yl)methanone;
and a veterinary acceptable salt thereof.

6. The composition of claim 4, wherein the composition further comprises at least one veterinary acceptable excipient.

7. The composition of claim 5, wherein the composition further comprises at least one veterinary acceptable excipient.

* * * * *